United States Patent
Schmidt et al.

(10) Patent No.: US 11,712,561 B2
(45) Date of Patent: Aug. 1, 2023

(54) ELECTRICAL STIMULATION WITH THERMAL TREATMENT OR THERMAL MONITORING

(71) Applicant: Boston Scientific Scimed, Inc., Maple Grove, MN (US)

(72) Inventors: Brian L. Schmidt, White Bear Lake, MN (US); Benjamin Keith Stein, Shoreview, MN (US); Keith R. Maile, New Brighton, MN (US); William J. Linder, Golden Valley, MN (US); Aleksandra Kharam, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 524 days.

(21) Appl. No.: 16/855,448

(22) Filed: Apr. 22, 2020

(65) Prior Publication Data
US 2020/0338346 A1 Oct. 29, 2020

Related U.S. Application Data

(60) Provisional application No. 62/837,416, filed on Apr. 23, 2019.

(51) Int. Cl.
*A61N 1/36* (2006.01)
*A61F 7/00* (2006.01)

(52) U.S. Cl.
CPC .......... *A61N 1/36002* (2017.08); *A61F 7/007* (2013.01); *A61F 2007/0073* (2013.01); *A61F 2007/0096* (2013.01)

(58) Field of Classification Search
None
See application file for complete search history.

(56) References Cited

U.S. PATENT DOCUMENTS

| 4,016,886 A | 4/1977 | Doss et al. |
| 5,099,838 A | 3/1992 | Bardy |

(Continued)

FOREIGN PATENT DOCUMENTS

| AU | 2005301103 | 5/2006 |
| CN | 101693875 | 4/2010 |

(Continued)

OTHER PUBLICATIONS

"Optune®—Elevate Expectations / Patient Information and Operation Manual," Novocure™, www.optune.com, 46, pages, Jan. 2019.

(Continued)

*Primary Examiner* — Ankit D Tejani
(74) *Attorney, Agent, or Firm* — Pauly, DeVries Smith & Deffner LLC

(57) ABSTRACT

Embodiments herein relate to medical devices and methods for using the same to treat cancerous tumors within a bodily tissue. A medical device system is included having an electric field generating circuit configured to generate one or more electric fields and a control circuit in communication with the electric field generating circuit. The control circuit configured to control delivery of the one or more electric fields from the electric field generating circuit. The system can include two or more electrodes to deliver the electric fields to a site of a cancerous tumor within a patient and a temperature sensor to measure the temperature of tissue at the site of the cancerous tumor. The control circuit can cause the electric field generating circuit to generate one or more electric fields at frequencies selected from a range of between 10 kHz to 1 MHz. Other embodiments are also included herein.

5 Claims, 11 Drawing Sheets

(56) References Cited

U.S. PATENT DOCUMENTS

| | | |
|---|---|---|
| 5,324,328 A | 6/1994 | Li et al. |
| 5,397,342 A | 3/1995 | Heil et al. |
| 5,458,597 A | 10/1995 | Edwards et al. |
| 5,582,609 A | 12/1996 | Swanson et al. |
| 5,834,051 A | 11/1998 | Woloszko et al. |
| 6,366,808 B1 | 4/2002 | Schroeppel et al. |
| 6,673,623 B1 | 1/2004 | Huberman |
| 6,868,289 B2 | 3/2005 | Palti |
| 6,920,361 B2 | 7/2005 | Williams |
| 7,524,274 B2 | 4/2009 | Patrick et al. |
| 7,565,205 B2 | 7/2009 | Palti |
| 7,656,205 B2 | 2/2010 | Chen et al. |
| 7,715,921 B2 | 5/2010 | Palti |
| 7,720,549 B2 | 5/2010 | Schroeppel et al. |
| 7,805,201 B2 | 9/2010 | Palti |
| 7,809,441 B2 | 10/2010 | Kane et al. |
| 7,890,183 B2 | 2/2011 | Palti et al. |
| 7,917,227 B2 | 3/2011 | Palti |
| 8,002,821 B2 | 8/2011 | Stinson |
| 8,019,414 B2 | 9/2011 | Palti |
| 8,170,648 B2 | 5/2012 | Field et al. |
| 8,175,698 B2 | 5/2012 | Palti et al. |
| 8,229,555 B2 | 7/2012 | Palti |
| RE43,618 E | 8/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,483,821 B2 | 7/2013 | Averina et al. |
| 8,500,713 B2 | 8/2013 | Ferek-petric |
| 8,706,261 B2 | 4/2014 | Palti |
| 8,715,203 B2 | 5/2014 | Palti |
| 8,718,756 B2 | 5/2014 | Palti |
| 8,764,675 B2 | 7/2014 | Palti |
| 8,956,352 B2 | 2/2015 | Mauch et al. |
| 9,005,100 B2 | 4/2015 | Gnanashanmugam et al. |
| 9,023,090 B2 | 5/2015 | Palti |
| 9,023,091 B2 | 5/2015 | Palti |
| 9,039,674 B2 | 5/2015 | Palti et al. |
| 9,056,203 B2 | 6/2015 | Palti et al. |
| 9,248,278 B2 | 2/2016 | Crosby et al. |
| 9,283,383 B2 | 3/2016 | Osypka |
| 9,308,039 B2 | 4/2016 | Azure |
| 9,387,323 B2 | 7/2016 | Fleischhacker et al. |
| 9,440,068 B2 | 9/2016 | Palti et al. |
| 9,526,911 B1 | 12/2016 | Azure et al. |
| 9,630,022 B2 | 4/2017 | Bourke et al. |
| 9,655,669 B2 | 5/2017 | Palti et al. |
| 9,750,934 B2 | 9/2017 | Palti et al. |
| 9,833,617 B2 | 12/2017 | Travers et al. |
| 9,910,453 B2 | 3/2018 | Wasserman et al. |
| 10,029,117 B2 | 7/2018 | Bourke |
| 10,238,862 B2 | 3/2019 | Cook et al. |
| 10,265,530 B1 | 4/2019 | Perryman et al. |
| 10,376,177 B2 | 8/2019 | Valvano et al. |
| 10,471,254 B2 | 11/2019 | Sano et al. |
| 11,191,956 B2 | 12/2021 | Giladi et al. |
| 11,331,493 B2 | 5/2022 | Pivonka et al. |
| 11,338,135 B2 | 5/2022 | Schmidt et al. |
| 11,420,049 B2 | 8/2022 | Schmidt et al. |
| 2001/0044643 A1 | 11/2001 | Litovitz |
| 2002/0049485 A1 | 4/2002 | Smits |
| 2003/0020416 A1 | 1/2003 | Kobayashi |
| 2003/0069623 A1 | 4/2003 | Stypulkowski |
| 2003/0204161 A1 | 10/2003 | Ferek-Petric |
| 2004/0010290 A1 | 1/2004 | Schroeppel et al. |
| 2004/0158288 A1 | 8/2004 | Keisari et al. |
| 2004/0176804 A1 | 9/2004 | Palti |
| 2004/0215296 A1 | 10/2004 | Ganz et al. |
| 2005/0004507 A1 | 1/2005 | Schroeppel et al. |
| 2005/0043894 A1 | 2/2005 | Fernandez |
| 2005/0096584 A1 | 5/2005 | Ferek-petric |
| 2005/0209642 A1 | 9/2005 | Palti |
| 2005/0222623 A1 | 10/2005 | Kroll et al. |
| 2005/0222646 A1 | 10/2005 | Kroll et al. |
| 2005/0240173 A1 | 10/2005 | Palti |
| 2005/0288730 A1 | 12/2005 | Deem et al. |
| 2006/0024802 A1 | 2/2006 | Muller et al. |
| 2006/0149341 A1 | 7/2006 | Palti |
| 2006/0282122 A1 | 12/2006 | Palti |
| 2007/0033660 A1 | 2/2007 | Palti |
| 2007/0179550 A1 | 8/2007 | Dennis et al. |
| 2007/0225766 A1 | 9/2007 | Palti |
| 2007/0239213 A1 | 10/2007 | Palti |
| 2007/0239244 A1 | 10/2007 | Morgan et al. |
| 2007/0270675 A1 | 11/2007 | Kane et al. |
| 2007/0270916 A1 | 11/2007 | Fischell et al. |
| 2008/0058669 A1 | 3/2008 | Kroll |
| 2008/0071350 A1 | 3/2008 | Stinson et al. |
| 2008/0086073 A1 | 4/2008 | McDaniel |
| 2008/0195227 A1 | 8/2008 | Boling et al. |
| 2008/0208271 A1 | 8/2008 | Sih et al. |
| 2008/0275524 A1 | 11/2008 | Furness et al. |
| 2009/0076500 A1 | 3/2009 | Azure et al. |
| 2009/0192381 A1 | 7/2009 | Brockway et al. |
| 2009/0234211 A1 | 9/2009 | Li et al. |
| 2010/0016936 A1 | 1/2010 | Stevenson et al. |
| 2010/0198298 A1 | 8/2010 | Schulman et al. |
| 2010/0261994 A1 | 10/2010 | Davalos et al. |
| 2010/0298895 A1 | 11/2010 | Ghaffari et al. |
| 2010/0331938 A1 | 12/2010 | Sommer et al. |
| 2011/0125215 A1 | 5/2011 | Goetz et al. |
| 2011/0137229 A1 | 6/2011 | Palti et al. |
| 2011/0238057 A1 | 9/2011 | Moss et al. |
| 2012/0035616 A1 | 2/2012 | Olsen et al. |
| 2012/0130444 A1 | 5/2012 | Wei et al. |
| 2012/0158072 A1 | 6/2012 | Venook et al. |
| 2012/0158122 A1 | 6/2012 | Mattson et al. |
| 2012/0203307 A1 | 8/2012 | Schroeppel et al. |
| 2012/0232615 A1 | 9/2012 | Barolat et al. |
| 2012/0283726 A1 | 11/2012 | Palti |
| 2013/0023946 A1 | 1/2013 | Valvano et al. |
| 2013/0165916 A1 | 6/2013 | Mathur et al. |
| 2013/0204068 A1 | 8/2013 | Gnanashanmugam et al. |
| 2013/0261706 A1 | 10/2013 | Mirro et al. |
| 2013/0261711 A1 | 10/2013 | Sivo |
| 2013/0289649 A1 | 10/2013 | Averina et al. |
| 2013/0289664 A1 | 10/2013 | Johanek |
| 2013/0310898 A1 | 11/2013 | Ollivier et al. |
| 2014/0005753 A1 | 1/2014 | Carbunaru |
| 2014/0052227 A1 | 2/2014 | Wahlstrand et al. |
| 2014/0107511 A1 | 4/2014 | Banet et al. |
| 2014/0350653 A1 | 11/2014 | Shiroff et al. |
| 2015/0005804 A1 | 1/2015 | Franano et al. |
| 2015/0066024 A1 | 3/2015 | Azure |
| 2015/0134022 A1 | 5/2015 | Lee et al. |
| 2015/0180161 A1 | 6/2015 | Olson et al. |
| 2015/0320995 A1 | 11/2015 | Nazareth et al. |
| 2015/0374992 A1 | 12/2015 | Crosby et al. |
| 2016/0022986 A1 | 1/2016 | Travers et al. |
| 2016/0029960 A1 | 2/2016 | Toth et al. |
| 2016/0068598 A1 | 3/2016 | Yan et al. |
| 2016/0082258 A1 | 3/2016 | Kramer et al. |
| 2016/0128767 A1 | 5/2016 | Azamian et al. |
| 2016/0129276 A1 | 5/2016 | Fried et al. |
| 2016/0250476 A1 | 9/2016 | Kaemmerer et al. |
| 2016/0250483 A1 | 9/2016 | Klimovitch et al. |
| 2016/0331459 A1 | 11/2016 | Townley et al. |
| 2016/0346536 A1 | 12/2016 | Palti et al. |
| 2017/0007310 A1 | 1/2017 | Rajagopalan et al. |
| 2017/0035496 A1 | 2/2017 | Nagale et al. |
| 2017/0049514 A1 | 2/2017 | Cosman |
| 2017/0105793 A1 | 4/2017 | Cao et al. |
| 2017/0120041 A1 | 5/2017 | Wenger et al. |
| 2017/0173340 A1 | 6/2017 | Gupte et al. |
| 2017/0189098 A1 | 7/2017 | Azure et al. |
| 2017/0215939 A1 | 8/2017 | Palti et al. |
| 2017/0251976 A1 | 9/2017 | Schouenborg |
| 2017/0266371 A1 | 9/2017 | Leonhardt et al. |
| 2017/0281934 A1 | 10/2017 | Giladi et al. |
| 2017/0281955 A1 | 10/2017 | Maile et al. |
| 2017/0312501 A1 | 11/2017 | Bornzin et al. |
| 2017/0333702 A1 | 11/2017 | Barner |

(56) References Cited

U.S. PATENT DOCUMENTS

| | | | |
|---|---|---|---|
| 2018/0001075 A1 | 1/2018 | Kirson et al. |
| 2018/0001078 A1 | 1/2018 | Kirson et al. |
| 2018/0008708 A1 | 1/2018 | Giladi et al. |
| 2018/0021563 A1 | 1/2018 | Van De Stolpe et al. |
| 2018/0050200 A1 | 2/2018 | Wasserman et al. |
| 2018/0110978 A1 | 4/2018 | Beebe et al. |
| 2018/0154142 A1 | 6/2018 | Guo et al. |
| 2018/0221088 A1 | 8/2018 | Govari et al. |
| 2018/0246079 A1 | 8/2018 | Wang et al. |
| 2018/0289954 A1 | 10/2018 | Hebb et al. |
| 2019/0117969 A1 | 4/2019 | Schmidt et al. |
| 2019/0117970 A1 | 4/2019 | Schmidt et al. |
| 2019/0117971 A1 | 4/2019 | Schmidt et al. |
| 2019/0117972 A1 | 4/2019 | Schmidt et al. |
| 2019/0117973 A1 | 4/2019 | Schmidt et al. |
| 2019/0255344 A1 | 8/2019 | Carter et al. |
| 2020/0009377 A1 | 1/2020 | Chang et al. |
| 2020/0330756 A1 | 10/2020 | Schmidt et al. |
| 2020/0330757 A1 | 10/2020 | Schmidt et al. |
| 2020/0330758 A1 | 10/2020 | Schmidt et al. |
| 2020/0338344 A1 | 10/2020 | Schmidt et al. |
| 2020/0338345 A1 | 10/2020 | Schmidt et al. |
| 2021/0260370 A1 | 8/2021 | Srivastava et al. |
| 2022/0241586 A1 | 8/2022 | Spehr et al. |
| 2022/0296907 A1 | 9/2022 | Schmidt et al. |

FOREIGN PATENT DOCUMENTS

| | | |
|---|---|---|
| CN | 202365923 | 8/2012 |
| CN | 204698678 | 10/2015 |
| CN | 106823145 | 6/2017 |
| CN | 111263618 | 6/2020 |
| CN | 111263656 | 6/2020 |
| CN | 111278504 | 6/2020 |
| CN | 111432872 | 7/2020 |
| CN | 111465429 | 7/2020 |
| EP | 2942023 | 11/2015 |
| EP | 3700451 | 9/2020 |
| EP | 3700621 | 9/2020 |
| EP | 3700623 | 9/2020 |
| EP | 3700626 | 9/2020 |
| EP | 3700627 | 9/2020 |
| TW | 201039699 | 11/2010 |
| WO | 9513113 | 5/1995 |
| WO | 9526911 | 10/1995 |
| WO | 0158371 | 8/2001 |
| WO | 0167098 | 9/2001 |
| WO | 2005115535 | 12/2005 |
| WO | 2006047833 | 5/2006 |
| WO | 2008089360 | 7/2008 |
| WO | 2009036457 | 3/2009 |
| WO | 2009036459 | 3/2009 |
| WO | 2013052590 | 4/2013 |
| WO | 2015100451 | 7/2015 |
| WO | 2016065263 | 4/2016 |
| WO | 2016149575 | 9/2016 |
| WO | 2016168485 | 10/2016 |
| WO | 2016179712 | 11/2016 |
| WO | 2016199142 | 12/2016 |
| WO | 2017123981 | 7/2017 |
| WO | 2018207103 | 11/2018 |
| WO | 2019084003 | 5/2019 |
| WO | 2019084011 | 5/2019 |
| WO | 2019084013 | 5/2019 |
| WO | 2019084016 | 5/2019 |
| WO | 2019084021 | 5/2019 |
| WO | 2020219336 | 10/2020 |
| WO | 2020219337 | 10/2020 |
| WO | 2020219339 | 10/2020 |
| WO | 2020219517 | 10/2020 |
| WO | 2020219519 | 10/2020 |
| WO | 2020219521 | 10/2020 |

OTHER PUBLICATIONS

Di Sebastiano, Andrea R. et al., "Preclinical Outcomes of Intratumoral Modulation Therapy for Glioblastoma," Scientific Reports (2018) 8:7301 (11 pages).
File History for U.S. Appl. No. 16/166,957 downloaded Dec. 28, 2020 (427 pages).
File History for U.S. Appl. No. 16/167,079 downloaded Dec. 28, 2020 (301 pages).
File History for U.S. Appl. No. 16/167,087 downloaded Dec. 28, 2020 (310 pages).
File History for U.S. Appl. No. 16/167,116 downloaded Dec. 28, 2020 (238 pages).
File History for U.S. Appl. No. 16/167,140 downloaded Dec. 28, 2020 (231 pages).
"First Examination Report," for Australian Patent Application No. 2018354149 dated Jul. 29, 2020 (5 pages).
"First Examination Report," for Australian Patent Application No. 2018354157 dated Jul. 31, 2020 (5 pages).
"First Examination Report," for Australian Patent Application No. 2018354159 dated Aug. 12, 2020 (5 pages).
"First Examination Report," for Australian Patent Application No. 2018354162 dated Sep. 29, 20 (8 pages).
"First Examination Report," for Australian Patent Application No. 2018354167 dated Sep. 14, 2020 (5 pages).
"International Preliminary Report on Patentability," for PCT Application No. PCT/US2018/057104 dated May 7, 2020 (8 pages).
"International Preliminary Report on Patentability," for PCT Application No. PCT/US2018/057115 dated May 7, 2020 (9 pages).
"International Preliminary Report on Patentability," for PCT Application No. PCT/US2018/057117 dated May 7, 2020 (8 pages).
"International Preliminary Report on Patentability," for PCT Application No. PCT/US2018/057120 dated May 7, 2020 (8 pages).
"International Preliminary Report on Patentability," for PCT Application No. PCT/US2018/057127 dated May 7, 2020 (8 pages).
"International Search Report and Written Opinion," for PCT Application No. PCT/US2018/057104 dated Dec. 20, 2018 (14 pages).
"International Search Report and Written Opinion," for PCT Application No. PCT/US2018/057115 dated Jan. 4, 2019 (13 pages).
"International Search Report and Written Opinion," for PCT Application No. PCT/US2018/057117 dated Dec. 20, 2018 (14 pages).
"International Search Report and Written Opinion," for PCT Application No. PCT/US2018/057120 dated Dec. 19, 2018 (14 pages).
"International Search Report and Written Opinion," for PCT Application No. PCT/US2018/057127 dated Jan. 18, 2019 (12 pages).
"International Search Report and Written Opinion," for PCT Application No. PCT/US2020/028508 dated Aug. 3, 2020 (13 pages).
"International Search Report and Written Opinion," for PCT Application No. PCT/US2020/028509 dated Jun. 30, 2020 (15 pages).
"International Search Report and Written Opinion," for PCT Application No. PCT/US2020/028512 dated Jul. 13, 2020 (14 pages).
"International Search Report and Written Opinion," for PCT Application No. PCT/US2020/029270 dated Oct. 26, 2020 (19 pages).
"International Search Report and Written Opinion," for PCT Application No. PCT/US2020/029274 dated Aug. 28, 2020 (19 pages).
"International Search Report and Written Opinion," for PCT Application No. PCT/US2020/029277 dated Jul. 13, 2020 (15 pages).
"Invitation to Pay Additional Fees," for PCT Application No. PCT/US2020/029270 mailed Aug. 28, 2020 (14 pages).
"Invitation to Pay Additional Fees," for PCT Application No. PCT/US2020/029274 mailed Jul. 7, 2020 (13 pages).
Kirson, Eilon D. et al., "Disruption of Cancer Cell Replication by Alternating Electric Fields," Cancer Research 64, 3288-3295, May 1, 2004 (8 pages).
"Novocure Announces Launch of the inovitro™," Laboratory Research System, Press Release, 2 pages, Nov. 21, 2013., 2 pages.
"Response to Communication Pursuant to Rules 161(1) and 162 EPC," for European Patent Application No. 18800411.3 filed Dec. 9, 2020 (11 pages).
"Response to Communication Pursuant to Rules 161(1) and 162 EPC," for European Patent Application No. 18801134.0 filed Dec. 11, 2020 (9 pages).

(56) References Cited

OTHER PUBLICATIONS

"Response to Communication Pursuant to Rules 161(1) and 162 EPC," for European Patent Application No. 18801136.5 filed Dec. 10, 2020 (8 pages).
"Response to Communication Pursuant to Rules 161(1) and 162 EPC," for European Patent Application No. 18801137.3 filed Dec. 10, 2020 (7 pages).
"Response to Communication Pursuant to Rules 161(1) and 162 EPC," for European Patent Application No. 18801138.1 filed Dec. 11, 2020 (16 pages).
"Response to Examination Report," for Australian Patent Application No. 2018354149 filed Dec. 21, 2020 (14 pages).
Wang, Lijun et al., "Tumour Cell Membrane Poration and Ablation by Pulsed Low-Intensity Electric Field with Carbon Nanotubes," Int. J. Mol. Sci. 2015, 16, 6890-6901 (12 pages).
Xu, Hu et al., "In Vitro Validation of Intratumoral Modulation Therapy for Glioblastoma," Anticancer Research 36:71-80 (2016), 10 pages.
"Communication Pursuant to Article 94(3) EPC," for European Patent Application No. 18801137.3 dated Sep. 15, 2021 (4 pages).
"Decision of Rejection," for Japanese Patent Application No. 2020-542719 dated Oct. 19, 2021 (3 pages) No English Translation.
"First Office Action," for Chinese Patent Application No. 201880078117.8 dated Jul. 20, 2021 (14 pages) with English Summary.
"Non-Final Office Action," for U.S. Appl. No. 16/167,116 dated Sep. 3, 2021 (29 pages).
"Non-Final Office Action," for U.S. Appl. No. 16/850,720 dated Aug. 24, 2021 (32 pages).
"Non-Final Office Action," for U.S. Appl. No. 16/855,433 dated Sep. 8, 2021 (32 pages).
"Office Action," for Japanese Patent Application No. 2020-542718 dated Oct. 19, 2021 (3 pages) No English Translation.
"Office Action," for Japanese Patent Application No. 2020-542722 dated Oct. 26, 2021 (5 pages) No English Translation.
"Response to Communication Pursuant to Article 94(3) EPC," for European Patent Application No. 18801138.1 filed Oct. 15, 2021 (10 pages).
"Response to Final Rejection dated," Aug. 2, 2021 for U.S. Appl. No. 16/167,087, submitted via EFS-Web on Nov. 1, 2021, 12 pages.
"Response to Final Rejection," dated Jun. 23, 2021 and the Advisory Action dated Oct. 15, 2021 for U.S. Appl. No. 16/167,079, submitted via EFS-Web on Oct. 21, 2021, 19 pages.
"Response to Final Rejection," dated Jun. 23, 2021 for U.S. Appl. No. 16/167,079, submitted via EFS-Web on Sep. 9, 2021, 16 pages.
"Response to Final Rejection," dated May 14, 2021 and Advisory Action dated Aug. 26, 2021 for U.S. Appl. No. 16/166,957, submitted via EFS-Web on Sep. 10, 2021.
"Response to Non-Final Rejection," dated Aug. 24, 2021 for U.S. Appl. No. 16/850,720, submitted via EFS-Web on Nov. 1, 2021, 11 pages.
"Response to Non-Final Rejection," dated Jul. 12, 2021 for U.S. Appl. No. 16/167,140, submitted via EFS-Web on Oct. 12, 2021, 16 pages.
"Response to Non-Final Rejection," dated May 28, 2021 for U.S. Appl. No. 16/855,421, submitted via EFS-Web on Aug. 20, 2021, 11 pages.
"Response to Non-Final Rejection," dated Sep. 3, 2021 for U.S. Appl. No. 16/167,116, submitted via EFS-Web on Nov. 2, 2021, 14 pages.
"Response to Non-Final Rejection," dated Sep. 8, 2021 for U.S. Appl. No. 16/855,433, submitted via EFS-Web on Nov. 2, 2021, 12 pages.
"Response to Office Action," for Canadian Patent Application No. 3,079,289 filed with CIPO dated Sep. 23, 2021 (17 pages).
"Final Office Action," for U.S. Appl. No. 16/855,433 dated Feb. 1, 2022 (20 pages).
"Non-Final Office Action," for U.S. Appl. No. 16/850,712 dated Jan. 21, 2022 (40 pages).
"Non-Final Office Action," for U.S. Appl. No. 17/182,436 dated Feb. 1, 2022 (41 pages).
"Notice of Allowance," for U.S. Appl. No. 16/167,116 dated Jan. 26, 2022 (19 pages).
"Response to Communication Pursuant to Art. 94(3) EPC," for European Patent Application No. 18801137.3 filed Jan. 13, 2022 (8 pages).
"Response to Final Rejection," dated Dec. 27, 2021 for U.S. Appl. No. 16/167,140, submitted via EFS-Web on Feb. 9, 2022, 9 pages.
"Response to Final Rejection," dated Nov. 15, 2021 for U.S. Appl. No. 16/850,720, submitted via EFS-Web on Feb. 11, 2022, 12 pages.
"Communication Pursuant to Article 94(3) EPC," for European Patent Application No. 18801138.1 dated Aug. 29, 2022 (5 pages).
"Final Office Action," for U.S. Appl. No. 16/850,712 dated Jul. 5, 2022 (16 pages).
"Final Office Action," for U.S. Appl. No. 17/182,436 dated Jul. 27, 2022 (19 pages).
"International Preliminary Report on Patentability," for PCT Application No. PCT/US2021/019160 dated Sep. 9, 2022 (10 pages).
"International Search Report and Written Opinion," for PCT Application No. PCT/US2022/021161 dated Jun. 22, 2022 (15 pages).
"Non-Final Office Action," for U.S. Appl. No. 16/167,087 dated Sep. 15, 2022 (24 pages).
Notice of Opposition for European Patent No. 3700627 filed Aug. 24, 2022 (20 pages).
"Office Action Response," for Canadian Patent Application No. 3,079,289 filed Jul. 18, 2022 (17 pages).
"Office Action Response," for Canadian Patent Application No. 3,079,314 filed Aug. 11, 2022 (7 pages).
"Response to Final Rejection," dated Jul. 5, 2022 and Advisory Action dated Sep. 15, 2022 for U.S. Appl. No. 16/850,712, submitted via EFS-Web on Sep. 23, 2022, 10 pages.
"Response to Final Rejection," dated Jul. 5, 2022 for U.S. Appl. No. 16/850,712, submitted via EFS-Web on Sep. 6, 2022, 10 pages.
"Response to Final Rejection," dated May 18, 2022 for U.S. Appl. No. 16/166,957, submitted via EFS-Web on Aug. 18, 2022, 14 pages.
"Response to Final Rejection," dated May 18, 2022 for U.S. Appl. No. 16/167,087, submitted via EFS-Web on Aug. 18, 2022, 9 pages.
"Response to Final Rejection," dated May 27, 2022 for U.S. Appl. No. 16/167,079, submitted via EFS-Web on Aug. 26, 2022, 12 pages.
"Response to Non-Final Rejection," dated Jun. 7, 2022 for U.S. Appl. No. 16/855,421, submitted via EFS-Web on Sep. 7, 2022, 9 pages.
"Response to Non-Final Rejection," dated May 27, 2022 for U.S. Appl. No. 16/167,140, submitted via EFS-Web on Aug. 25, 2022, 14 pages.
"Response to Non-Final Rejection," dated May 27, 2022 for U.S. Appl. No. 16/855,433, submitted via EFS-Web on Aug. 25, 2022, 9 pages.
"Response to Office Action," for Canadian Patent Application No. 3,079,213 filed Aug. 10, 2022 (10 pages).
"Third Office Action," for Japanese Patent Application No. 2020-542721 dated Aug. 23, 2022 (9 pages) with English translation.
Notice of Opposition for European Patent Application No. 18801134.0 on behalf of Novocure Gmbh, dated Jun. 28, 2022 (36 pages).
"Communication Pursuant to Article 94(3) EPC," for European Patent Application No. 18801138.1 dated Jun. 7, 2021 (7 pages).
"Examination Report," for Australian Patent Application No. 2018354162 dated Apr. 21, 2021 (5 pages).
"Examination Report," for Canadian Patent Application No. 3,079,213 dated Jul. 12, 2021 (4 pages).
"Examination Report," for Canadian Patent Application No. 3,079,282 dated Jul. 14, 2021 (4 pages).
"Examination Report," for Canadian Patent Application No. 3,079,314 dated Jul. 14, 2021 (4 pages).
"Final Office Action," for U.S. Appl. No. 16/166,957 dated May 14, 2021 (33 pages).
"Final Office Action," for U.S. Appl. No. 16/167,079 dated Jun. 23, 2021 (34 pages).

(56) References Cited

OTHER PUBLICATIONS

"Final Office Action," for U.S. Appl. No. 16/167,087 dated Aug. 2, 2021 (25 pages).
"First Office Action," for Chinese Patent Application No. 201880068896.3 dated Apr. 13, 2021 (17 pages) with English Summary.
"International Search Report and Written Opinion," for PCT Application No. PCT/US2021/019160 dated Jun. 2, 2021 (15 pages).
"Non-Final Office Action," for U.S. Appl. No. 16/167,140 dated Jul. 12, 2021 (32 pages).
"Non-Final Office Action," for U.S. Appl. No. 16/855,421 dated May 28, 2021 (37 pages).
"Office Action," for Canadian Patent Application No. 3,079,289 dated May 28, 2021 (4 pages).
"Office Action," for Japanese Patent Application No. 2020-542719 dated Jun. 1, 2021 (9 pages) with English Translation.
"Office Action," for Japanese Patent Application No. 2020-542720 dated May 11, 2021 (13 pages) with English Translation.
"Response to Examination Report," for Australian Patent Application No. 2018354162 filed Jul. 13, 2021 (18 pages).
"Response to Final Rejection," dated May 14, 2021 for U.S. Appl. No. 16/166,957, submitted via EFS-Web on Aug. 5, 2021, 18 pages.
"Response to Non-Final Rejection," dated Mar. 31, 2021 for U.S. Appl. No. 16/167,087, submitted via EFS-Web on Jun. 23, 2021, 12 pages.
"Final Office Action," for U.S. Appl. No. 16/166,957 dated May 18, 2022 (35 pages).
"Final Office Action," for U.S. Appl. No. 16/167,079 dated May 27, 2022 (29 pages).
"Final Office Action," for U.S. Appl. No. 16/167,087 dated May 18, 2022 (26 pages).
"Non-Final Office Action," for U.S. Appl. No. 16/167,079 dated Feb. 17, 2022 (37 pages).
"Non-Final Office Action," for U.S. Appl. No. 16/167,140 dated May 27, 2022 (25 pages).
"Non-Final Office Action," for U.S. Appl. No. 16/855,421 dated Jun. 7, 2022 (21 pages).
"Non-Final Office Action," for U.S. Appl. No. 16/855,433 dated May 27, 2022 (18 pages).
"Notice of Allowance," for U.S. Appl. No. 16/850,720 dated Apr. 14, 2022 (17 pages).
"Office Action," for Canadian Patent Application No. 3,079,213 dated Apr. 20, 2022 (6 pages).
"Office Action," for Canadian Patent Application No. 3,079,289 dated Mar. 24, 2022 (8 pages).
"Office Action," for Canadian Patent Application No. 3,079,314 dated Apr. 29, 2022 (3 pages).
"Response to Communication Pursuant to Rules 161(1) and 162 EPC," for European Patent Application No. 20724332.0 filed May 11, 2022 (24 pages).
"Response to Communication Pursuant to Rules 161(1) and 162 EPC," for European Patent Application No. 20724702.4 filed May 11, 2022 (24 pages).
"Response to Communication Pursuant to Rules 161(1) and 162 EPC," for European Patent Application No. 20724703.2 filed Jun. 8, 2022 (12 pages).
"Response to Communication Pursuant to Rules 161(1) and 162 EPC," for European Patent Application No. 20727417.6 filed Jun. 1, 2022 (8 pages).
"Response to Communication Pursuant to Rules 161(1) and 162 EPC," for European Patent Application No. 20724333.8 filed Jun. 8, 2022 (8 pages).
"Response to Final Rejection," dated Dec. 27, 2021 and Advisory Action dated Mar. 9, 2022 for U.S. Appl. No. 16/167,140, submitted via EFS-Web on Mar. 25, 2022, 11 pages.
"Response to Final Rejection," dated Feb. 1, 2022 for U.S. Appl. No. 16/855,433, submitted via EFS-Web on May 2, 2022, 9 pages.
"Response to Final Rejection," dated Nov. 5, 2021 and Advisory Action dated Feb. 9, 2022 for U.S. Appl. No. 16/855,421, submitted via EFS-Web on Mar. 4, 2022, 11 pages.

"Response to Non-Final Rejection," dated Dec. 22, 2021 for U.S. Appl. No. 16/166,957, submitted via EFS-Web on Mar. 22, 2022, 13 pages.
"Response to Non-Final Rejection," dated Dec. 22, 2021 for U.S. Appl. No. 16/167,087, submitted via EFS-Web on Mar. 22, 2022, 9 pages.
"Response to Non-Final Rejection," dated Feb. 1, 2022 for U.S. Appl. No. 17/182,436, submitted via EFS-Web on Mar. 21, 2022, 8 pages.
"Response to Non-Final Rejection," dated Feb. 17, 2022 for U.S. Appl. No. 16/167,079, submitted via EFS-Web on May 3, 2022, 11 pages.
"Response to Non-Final Rejection," dated Jan. 21, 2022 for U.S. Appl. No. 16/850,712, submitted via EFS-Web on Mar. 21, 2022, 10 pages.
"Office Action," for Canadian Patent Application No. 3,079,316 dated Jun. 3, 2022 (3 pages).
"Decision of Rejection," for Japanese Patent Application No. 2020-54219 dated Oct. 19, 2021 (6 pages) with English Translation.
"Final Office Action," for U.S. Appl. No. 16/167,140 dated Dec. 27, 2021 (30 pages).
"Final Office Action," for U.S. Appl. No. 16/850,720 dated Nov. 15, 2021 (15 pages).
"Final Office Action," for U.S. Appl. No. 16/855,421 dated Nov. 5, 2021 (25 pages).
"International Preliminary Report on Patentability," for PCT Application No. PCT/US2020/028508 dated Nov. 4, 2021 (8 pages).
"International Preliminary Report on Patentability," for PCT Application No. PCT/US2020/028509 dated Nov. 4, 2021 (9 pages).
"International Preliminary Report on Patentability," for PCT Application No. PCT/US2020/028512 dated Nov. 4, 2021 (8 pages).
"International Preliminary Report on Patentability," for PCT Application No. PCT/US2020/029270 dated Nov. 4, 2021 (11 pages).
"International Preliminary Report on Patentability," for PCT Application No. PCT/US2020/029274 dated Nov. 4, 2021 (13 pages).
"International Preliminary Report on Patentability," for PCT Application No. PCT/US2020/029277 dated Nov. 4, 2021 (10 pages).
"Non-Final Office Action," for U.S. Appl. No. 16/166,957 dated Dec. 22, 2021 (39 pages).
"Non-Final Office Action," for U.S. Appl. No. 16/167,087 dated Dec. 22, 2021 (24 pages).
"Office Action," for Canadian Patent Application No. 3,079,316 dated Oct. 27, 2021 (4 pages).
"Office Action," for Japanese Patent Application No. 2020-542721 dated Jan. 4, 2022 (2 pages) No English Translation.
"Response to Examination Report," for Canadian Patent Application No. 3,079,213 filed Nov. 10, 2021 (13 pages).
"Response to Examination Report," for Canadian Patent Application No. 3,079,282 filed Nov. 10, 2021 (13 pages).
"Response to Final Rejection," dated Nov. 5, 2021 for U.S. Appl. No. 16/855,421, submitted via EFS-Web on Jan. 5, 2022, 11 pages.
"Response to Office Action," for Canadian Patent Application No. 3,079,314 filed Nov. 12, 2021 (14 pages).
"Response to Office Action," for Canadian Patent Application No. 3,079,316 filed Dec. 31, 2021 (15 pages).
"Second Office Action," for Chinese Patent Application No. 201880068896.3 dated Oct. 20, 2021 (6 pages), no English translation.
"Communication Pursuant to Article 94(3) EPC," for European Patent Application No. 18801137.3 dated Mar. 5, 2021 (4 pages).
"Examination Report," for Australian Patent Application No. 2018354162 dated Feb. 4, 2021 (5 pages).
"Final Office Action," for U.S. Appl. No. 16/167,116 dated Jan. 21, 2021 (25 pages).
Giladi, Moshe et al., "Mitotic Spindle Disruption by Alternating Electric Fields Leads to Improper Chromosome Segregation and Mitotic Catastrophe in Cancer Cells," Sci Rep 5, 18046 (2016), 16 pages.
"Non-Final Office Action," for U.S. Appl. No. 16/166,957 dated Feb. 17, 2021 (37 pages).
"Non-Final Office Action," for U.S. Appl. No. 16/167,079 dated Jan. 6, 2021 (28 pages).

(56) References Cited

OTHER PUBLICATIONS

"Non-Final Office Action," for U.S. Appl. No. 16/167,087 dated Mar. 31, 2021 (28 pages).
"Office Action," for Japanese Patent Application No. 2020-542718 dated Feb. 9, 2021 11 pages) with English Translation.
"Office Action," for Japanese Patent Application No. 2020-542721 dated Feb. 9, 2021 (10 pages) with English Summary.
"Office Action," for Japanese Patent Application No. 2020-542722 dated Feb. 9, 2021 (5 pages) with English Summary.
"Response to Examination Report," for Australian Patent Application No. 2018354157 filed Dec. 31, 2020 (17 pages).
"Response to Examination Report," for Australian Patent Application No. 2018354159 filed Jan. 18, 2021 (21 pages).
"Response to Examination Report," for Australian Patent Application No. 2018354162 filed Jan. 28, 2021 (15 pages).
"Response to Examination Report," for Australian Patent Application No. 2018354162 filed Mar. 30, 2021 (15 pages).
"Response to Examination Report," for Australian Patent Application No. 2018354167 filed Jan. 28, 2021 (17 pages).
"Response to Final Rejection," dated Jan. 21, 2021 for U.S. Appl. No. 16/167,116, submitted via EFS-Web on Mar. 2, 2021, 12 pages.
"Response to Final Rejection," dated Oct. 13, 2020 for U.S. Appl. No. 16/167,087, 11 pages, submitted via EFS-Web on Jan. 13, 2021.
"Response to Final Rejection," dated Oct. 19, 2020 for U.S. Appl. No. 16/167,140, submitted via EFS-Web on Jan. 19, 2021, 16 pages.
"Response to Non-Final Rejection," dated Feb. 17, 2021 for U.S. Appl. No. 16/166,957, submitted via EFS-Web on Mar. 17, 2021, 17 pages.
"Response to Non-Final Rejection," dated Jan. 6, 2021 for U.S. Appl. No. 16/267,079, submitted via EFS-Web on Apr. 6, 2021, 19 pages.
"Response to Non-Final Rejection," dated Oct. 7, 2020 for U.S. Appl. No. 16/167,116, submitted via EFS-Web on Jan. 6, 2021, 13 pages.
"Response to Second Examination Report," for Australian Patent Application No. 2018354149 filed Apr. 13, 2021 (19 pages).
"Second Examination Report," for Australian Patent Application No. 2018354149 dated Jan. 8, 2021 (4 pages).
"Communication Pursuant to Article 94(3) EPC," for European Patent Application No. 18800411.3 dated Dec. 22, 2022 (5 pages).
"Non-Final Office Action," for U.S. Appl. No. 16/850,728 dated Jan. 24, 2023 (68 pages).
"Office Action,"for Canadian Patent Application No. 3,079,213 dated Dec. 5, 2022 (4 pages).
"Office Action,"for Japanese Patent Application No. 2021-562797 dated Nov. 22, 2022 (9 pages), with English Translation.
"Office Action,"for Japanese Patent Application No. 2021-562966 dated Nov. 29, 2022 (8 pages) with English Translation.
"Office Action,"for Japanese Patent Application No. 2021-562972 dated Nov. 8, 2022 (26 pages) with English Translation.
"Response to Communication Pursuant to Rules 161(1) and 162 EPC," for European Patent Application No. 21712639.0 filed Jan. 20, 2023 (26 pages).
"Response to Non-Final Rejection," dated Oct. 6, 2022 for U.S. Appl. No. 16/850,712, submitted via EFS-Web on Jan. 4, 2023, 10 pages.
"First Office Action," for Chinese Patent Application No. 201880068897.8 dated Sep. 21, 2022 (11 pages) with English Summary.
"Non-Final Office Action," for U.S. Appl. No. 16/166,957 dated Sep. 29, 2022 (41 pages).
"Non-Final Office Action," for U.S. Appl. No. 16/167,140 dated Nov. 15, 2022 (29 pages).
"Non-Final Office Action," for U.S. Appl. No. 16/850,712 dated Oct. 6, 2022 (11 pages).
"Non-Final Office Action," for U.S. Appl. No. 16/855,433 dated Nov. 17, 2022 (39 pages).
"Non-Final Office Action," for U.S. Appl. No. 17/182,436 dated Nov. 23, 2022 (19 pages).
"Notice of Allowance,"for U.S. Appl. No. 16/855,421 dated Nov. 16, 2022 (17 pages).
"Office Action," for Canadian Patent Application No. 3,079,289 dated Nov. 28, 2022 (7 pages).
"Office Action," for Japanese Patent Application No. 2021-562795 dated Nov. 15, 2022 (5 pages), with English Translation.
"Office Action," for Japanese Patent Application No. 2021-562798 dated Nov. 15, 2022 (14 pages), with English translation.
"Response to Final Rejection," dated Jul. 22, 2022 with Request for Continued Examination, for U.S. Appl. No. 17/182,436, submitted via EFS-Web on Sep. 29, 2022, 9 pages.
"Response to Final Rejection," dated Jul. 27, 2022 for U.S. Appl. No. 17/182,436, submitted via EFS-Web on Sep. 27, 2022, 9 pages.
"Response to Non-Final Rejection," dated Sep. 15, 2022 for U.S. Appl. No. 16/167,087, submitted via EFS-Web on Dec. 13, 2022, 8 pages.
"Response to Non-Final Rejection," dated Sep. 29, 2022 for U.S. Appl. No. 16/166,957, submitted via EFS-Web on Dec. 13, 2022, 16 pages.

ELECTRICAL STIMULATION WITH THERMAL TREATMENT OR THERMAL MONITORING

This application claims the benefit of U.S. Provisional Application No. 62/837,416, filed Apr. 23, 2019, the content of which is herein incorporated by reference in its entirety.

FIELD

Embodiments herein relate to medical devices and methods for using the same to treat cancerous tumors within a bodily tissue.

BACKGROUND

According to the American Cancer Society, cancer accounts for nearly 25% of the deaths that occur in the United States each year. The current standard of care for cancerous tumors can include first-line therapies such as surgery, radiation therapy, and chemotherapy. Additional second-line therapies can include radioactive seeding, cryotherapy, hormone or biologics therapy, ablation, and the like. Combinations of first-line therapies and second-line therapies can also be a benefit to patients if one particular therapy on its own is not effective.

Cancerous tumors can form if one normal cell in any part of the body mutates and then begins to grow and multiply too much and too quickly. Cancerous tumors can be a result of a genetic mutation to the cellular DNA or RNA that arises during cell division, an external stimulus such as ionizing or non-ionizing radiation, exposure to a carcinogen, or a result of a hereditary gene mutation. Regardless of the etiology, many cancerous tumors are the result of unchecked rapid cellular division.

SUMMARY

In a first aspect, a medical device system is included having an electric field generating circuit configured to generate one or more electric fields and a control circuit in communication with the electric field generating circuit. The control circuit can be configured to control delivery of the one or more electric fields from the electric field generating circuit. The system can include two or more electrodes to deliver the electric fields to a site of a cancerous tumor within a patient and a temperature sensor to measure the temperature of tissue at the site of the cancerous tumor, the temperature sensor in electronic communication with the control circuit. The control circuit can cause the electric field generating circuit to generate one or more electric fields at frequencies selected from a range of between 10 kHz to 1 MHz.

In a second aspect, in addition to one or more of the preceding or following aspects, or in the alternative to some aspects, the system can include a first lead providing electrical communication between the control circuit and at least one electrode; wherein the temperature sensor is disposed on the first lead.

In a third aspect, in addition to one or more of the preceding or following aspects, or in the alternative to some aspects, the first lead can include at least one of a transcutaneous lead and a fully implanted lead.

In a fourth aspect, in addition to one or more of the preceding or following aspects, or in the alternative to some aspects, at least two electrodes are configured to be implanted.

In a fifth aspect, in addition to one or more of the preceding or following aspects, or in the alternative to some aspects, the electric fields are delivered across at least one vector defined by an electrode pair.

In a sixth aspect, in addition to one or more of the preceding or following aspects, or in the alternative to some aspects, the temperature sensor is positioned between the electrode pair.

In a seventh aspect, in addition to one or more of the preceding or following aspects, or in the alternative to some aspects, the temperature sensor is adapted to be inserted into the cancerous tumor.

In an eighth aspect, in addition to one or more of the preceding or following aspects, or in the alternative to some aspects, the electric fields are delivered across at least two vectors, wherein a first vector is defined by a first pair of electrodes and a second vector is defined by a second pair of electrodes.

In a ninth aspect, in addition to one or more of the preceding or following aspects, or in the alternative to some aspects, wherein the electric fields along the at least two vectors are spatially and/or directionally separated from one another.

In a tenth aspect, in addition to one or more of the preceding or following aspects, or in the alternative to some aspects, the system can include at least two electric field generating circuits, wherein a first electric field generating circuit is implanted and a second electric field generating circuit is external.

In an eleventh aspect, in addition to one or more of the preceding or following aspects, or in the alternative to some aspects, the system can further include an implanted housing, the implanted housing defining an interior volume into which the electric field generating circuit and the control circuit are disposed.

In a twelfth aspect, in addition to one or more of the preceding or following aspects, or in the alternative to some aspects, the temperature sensor is selected from the group consisting of a thermistor, a resistance thermometer, a thermocouple, and a semi-conductor based sensor.

In a thirteenth aspect, a medical device system is included having an electric field generating circuit configured to generate one or more electric fields and a control circuit in communication with the electric field generating circuit, the control circuit configured to control delivery of the one or more electric fields from the electric field generating circuit. The system can include two or more electrodes forming at least one electrode pair to deliver the electric fields to a site of a cancerous tumor within a patient. The control circuit can cause the electric field generating circuit to generate one or more electric fields at frequencies selected from a range of between 10 kHz to 1 MHz. The control circuit can calculate a power output of the electric field and estimate a temperature of tissue within the electric field based on the power output and a distance between the electrodes of the electrode pair.

In a fourteenth aspect, in addition to one or more of the preceding or following aspects, or in the alternative to some aspects, the medical device system is configured to receive data regarding the distance between the electrodes of the electrode pair.

In a fifteenth aspect, in addition to one or more of the preceding or following aspects, or in the alternative to some aspects, the medical device system is configured to estimate the distance between the electrodes of the electrode pair based on impedance data.

In a sixteenth aspect, a medical device system is included having an electric field generating circuit configured to generate one or more electric fields and a control circuit in communication with the electric field generating circuit, the control circuit configured to control delivery of the one or more electric fields from the electric field generating circuit. The system can further include two or more electrodes forming at least one electrode pair to deliver the electric fields to a site of a cancerous tumor within a patient and wherein the control circuit causes the electric field generating circuit to generate one or more electric fields at frequencies selected from a range of between 10 kHz to 1 MHz. The control circuit can estimate a temperature of tissue within the electric field based on an impedance measurement.

In a seventeenth aspect, in addition to one or more of the preceding or following aspects, or in the alternative to some aspects, the control circuit estimates a temperature of tissue within the electric field based on an impedance measurement and a distance between the electrodes of the electrode pair.

In an eighteenth aspect, in addition to one or more of the preceding or following aspects, or in the alternative to some aspects, the medical device system is configured to receive data regarding the distance between the electrodes of the electrode pair.

In a nineteenth aspect, in addition to one or more of the preceding or following aspects, or in the alternative to some aspects, the control circuit estimates changes in temperature of tissue within the electric field based on changes in measured impedance.

In a twentieth aspect, in addition to one or more of the preceding or following aspects, or in the alternative to some aspects, the system can further include a heating element, wherein the control circuit causes the heating element to generate heat.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

Figure 1:
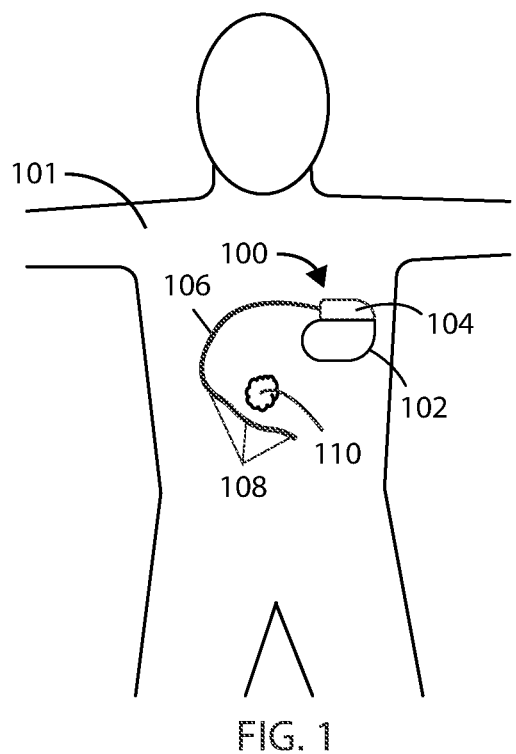
FIG. 1 is a schematic view of a medical system in accordance with various embodiments herein.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

As referenced above, many cancerous tumors can result from unchecked rapid cellular division. Some traditional first-line therapies to treat cancerous tumors can include surgery, radiation therapy, and chemotherapy. However, many first-line therapies have undesirable concomitant side effects, such as fatigue, hair loss, immunosuppression, and long surgical recovery times, to name a few.

While not intending to be bound by theory, it is believed that electric fields can disrupt mitosis within a cancerous tumor, such as by interfering with the dipole alignment of key proteins involved in cellular division; tubulin and septin in particular. The polymerization of tubulin proteins that form microtubule spindle fibers can be disrupted, thus preventing the formation of spindle fibers required for chromosome separation. This can halt cellular division at the metaphase stage of mitosis. In some instances, an electric field can halt polymerization of already growing spindle fibers, leading to incomplete spindles and unequal chromosome separation during anaphase, should the cell survive that long. In each case, halting microtubule spindle formation and unequal chromosome separation during anaphase caused by incomplete polymerization of microtubules, can result in apoptosis (i.e., programmed cell death). It is also believed that alternating electric fields can lead to increased electric field density near the cleavage furrow of the dividing cells during telophase. An increased electric field density in the region of the cleavage furrow can result in dielectrophoresis of charged macromolecules, such as proteins and nucleic acids, toward the high electric field density at the furrow. The unequal concentration of key macromolecules required for cellular division at the site of the cleavage furrow can disrupt the final separation of the sister cells during telophase and eventually lead to apoptosis.

Temperature can be in important parameter to measure during the administration of an electrical field. In some cases, it may be desirable to limit and/or prevent thermal destruction of tissues. As such, the temperature of tissue can be monitored (directly or indirectly) in order to prevent the temperature from rising to a level where the thermal destruction of tissue may occur. However, in some embodiments, a degree of heating in combination with the application of an electrical field may be therapeutic. Thus, in some embodiments, it may be desirable to apply heat to tissue.

As such, various embodiments disclosed herein include a medical device system that can generate an electric field for treatment of cancer that can include, or can control, at least one electrode, and/or at least one temperature sensor or at least one heating element. In various embodiments, an electric field can be generated, and heat can be applied, such as via a heating element, to treat a tumor. In various embodiments, a temperature sensor can be used to monitor the temperature of tissue near or around an electric field or a heating element, such as to observe changes to tissue during heating or electric field generation. In various embodiments, the medical device can be configured to turn off or stop the therapy if the temperature of the tissue exceed a threshold.

Referring now to FIG. 1, a schematic view is shown of a medical device 100 in accordance with various embodiments herein. The medical device 100 can be implanted entirely within the body of a patient 101 at or near the site of a cancerous tumor 110 located within a bodily tissue. Various implant sites can be used including areas such as in the limbs, the upper torso, the abdominal area, the head, and the like.

Figure 2:
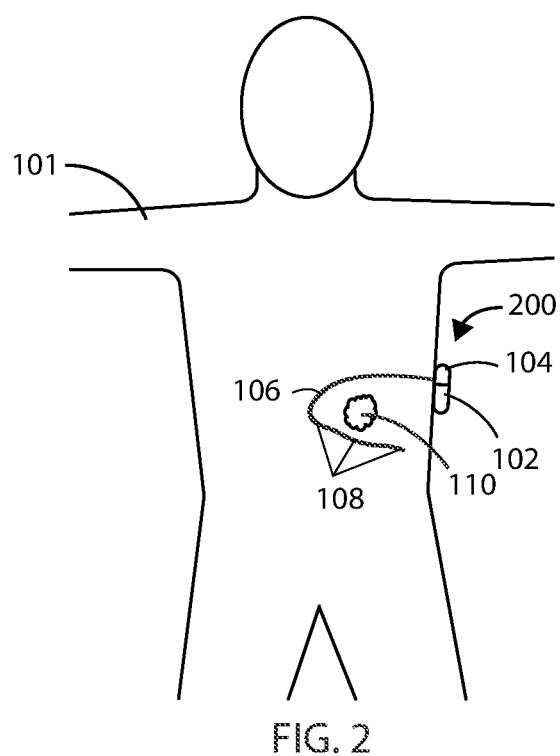
FIG. 2 is a schematic view of a medical system in accordance with various embodiments herein.

Referring now to FIG. 2, another schematic view is shown of a medical device 200 in accordance with various embodiments herein. The medical device 200 can be external but can be connected to a component, such as leads, that are at least partially implanted within the body of a patient 101. In some embodiments, the medical device 200 can be partially implanted and partially external to the body of a patient. In some embodiments, the medical device 200 can include a transcutaneous connection between components disposed internal to the body and external to the body. In various embodiments, the medical device system described herein can include an implanted medical device 100 and an external medical device 200. In other embodiments, the medical device system described herein can include a partially implanted medical device.

An implanted portion of a medical device system, such as an implanted medical device 100 or portion thereof, can wirelessly communicate patient identification data, diagnostic information, electric field data, physiological parameters, software updates, and the like with a fully or partially external portion of a medical device 200 over a wireless connection. Implanted medical device 100 can also wirelessly communicate with an external device configured to wirelessly charge the medical device utilizing inductance, radio frequency, and acoustic energy transfer techniques, and the like.

In some embodiments, a portion of a medical device or system can be entirely implanted, and a portion of the medical device can be entirely external. For example, in some embodiments, one or more electrodes or leads can be entirely implanted within the body, whereas the portion of the medical device that generates an electric field, such as an electric field generator, can be entirely external to the body. It will be appreciated that in some embodiments described herein, the electric field generators described can include many of the same components as and can be configured to perform many of the same functions as a pulse generator. In embodiments where a portion of a medical device is entirely implanted, and a portion of the medical device is entirely external, the portion of the medical device that is entirely external can communicate wirelessly with the portion of the medical device that is entirely internal. However, in other embodiments a wired connection can be used for the implanted portion to communication with the external portion.

The implanted medical device 100 and/or the medical device 200 can include a housing 102 and a header 104 coupled to the housing 102. Various materials can be used to form the housing 102. In some embodiments, the housing 102 can be formed of a material such as a metal, ceramic, polymer, composite, or the like. In some embodiments, the housing 102, or one or more portions thereof, can be formed of titanium. The header 104 can be formed of various materials, but in some embodiments the header 104 can be formed of a translucent polymer such as an epoxy material. In some embodiments the header 104 can be hollow. In other embodiments the header 104 can be filled with components and/or structural materials such as epoxy or another material such that it is non-hollow.

In some embodiments where a portion of the medical device 100 or 200 is partially external, the header 104 and housing 102 can be surrounded by a protective casing made of durable polymeric material. In other embodiments, where a portion of a device is partially external, the header 104 and housing 102 can be surrounded by a protective casing made of one or more of a polymeric material, metallic material, and/or glass material.

The header 104 can be coupled to one or more leads 106. The header 104 can serve to provide fixation of the proximal end of one or more leads 106 and electrically couple the one or more leads 106 to one or more components within the housing 102. The one or more leads 106 can include one or more electrodes 108 disposed along the length of the electrical leads 106. In some embodiments, electrodes 108 can include electric field generating electrodes and in other embodiments electrodes 108 can include electric field sensing electrodes. In some embodiments, leads 106 can include both electric field generating and electric field sensing electrodes. In other embodiments, leads 106 can include any number of electrodes that are both electric field sensing and electric field generating. The leads 106 can include one or more conductors therein, such as metal wires, to provide electrical communication between the electrodes and a proximal end (or plug) of the lead. The wires can exist as single strands or fibers or can be multifibrillar such as a cable. The leads 106 can include a shaft, typically formed of a polymeric material or another non-conductive material, within which the conductors therein can pass. The proximal end of the leads 106 can be inserted into the header 104, thereby providing electrical communication between the electrodes 108 and the components inside the housing 102. It will be appreciated that while many embodiments of medical devices herein are designed to function with leads, leadless medical devices that generate electrical fields are also contemplated herein.

In various embodiments, the electrodes 108 can be positioned around or adjacent to a tumor 110, such as a cancerous tumor. The tumor 110 can be positioned within an electric field generated by the electrodes 108.

The electric fields generated by the implanted medical device 100 and/or the medical device 200 can vary. In some embodiments, the implanted medical device 100 and/or the medical device 200 can generate one or more electric fields at frequencies selected from a range of between 10 kHz to 1 MHz.

Figure 3:
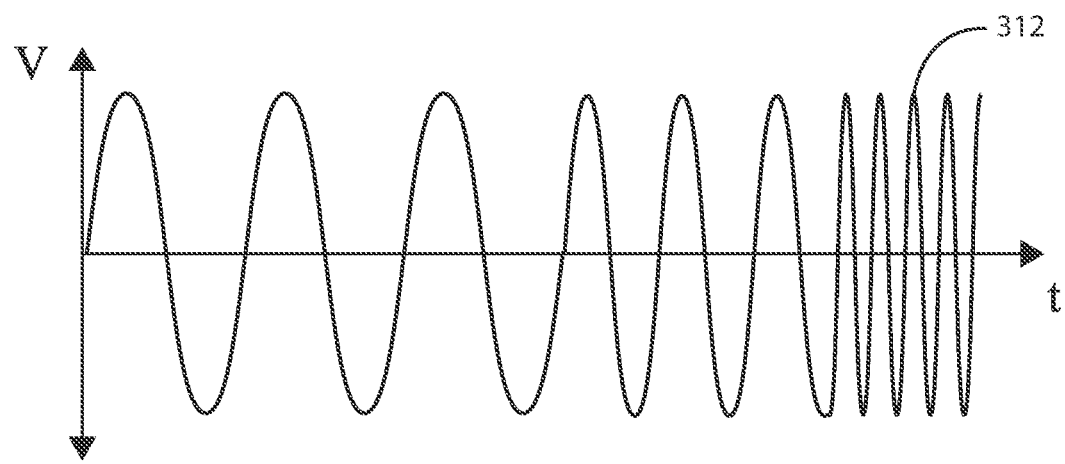
FIG. 3 is a plot of an exemplary therapy parameter in accordance with various embodiments herein.
Figure 4:
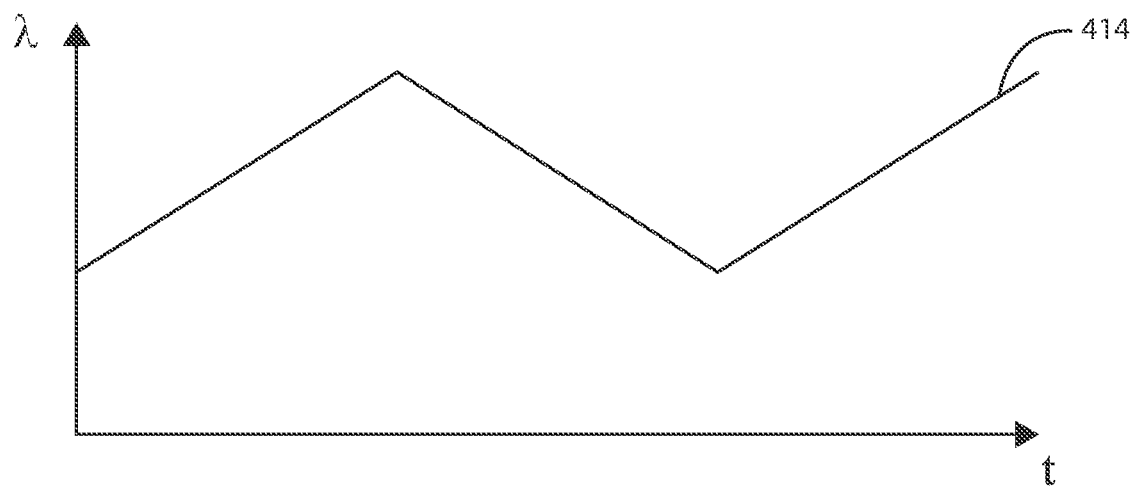
FIG. 4 is a plot of an exemplary therapy parameter in accordance with various embodiments herein.

In some embodiments, an electric field can be applied to the site of a cancerous tumor at a specific frequency or constant frequency range. However, in some embodiments, an electric field can be applied to the site of a cancerous tumor by sweeping through a range of frequencies. As one example, referring now to FIG. 3, exemplary plot 312 shows an alternating electric field, delivered by the electrodes 108, where the frequency increases over time. Similarly, FIG. 4 shows the change in frequency as a function of time in exemplary plot 414 during a programmed therapy parameter. In some embodiments, a frequency sweep can include sweeping from a minimum frequency up to a maximum frequency. In some embodiments, a frequency sweep can include sweeping from a maximum frequency down to a minimum frequency. In other embodiments, sweeping from a minimum frequency up to a maximum frequency and sweeping from the maximum frequency down to the minimum frequency can be repeated as many times as desired throughout the duration of the delivery of the electric field from the electric field generating circuit.

As therapy progresses during a frequency sweep, it may be desired to alternate between frequency ranges so that as the cells within a population change in size and number in response to therapy, more cells can be targeted. For example, in some embodiments, a frequency sweep can include alternating between a first frequency sweep covering a range of about 100 kHz to 300 kHz and a second frequency sweep covering a range about 200 kHz to 500 kHz. It will be appreciated that sweeping through a first and second frequency range as described can be performed indefinitely throughout the course of the therapy. In some embodiments, the second frequency sweep (range) can be at higher frequencies than the first frequency sweep (range). In some embodiments, the first frequency sweep (range) can be at higher frequencies than the second frequency sweep (range).

Frequency ranges for the first and second frequency ranges can be any range including specific frequencies recited above or below, provided that the lower end of each range is a value less than the upper end of each range. At times, it may be beneficial to have some amount of overlap between the frequency range of the first and second frequency sweep.

Medical Devices and Systems

Figure 5:
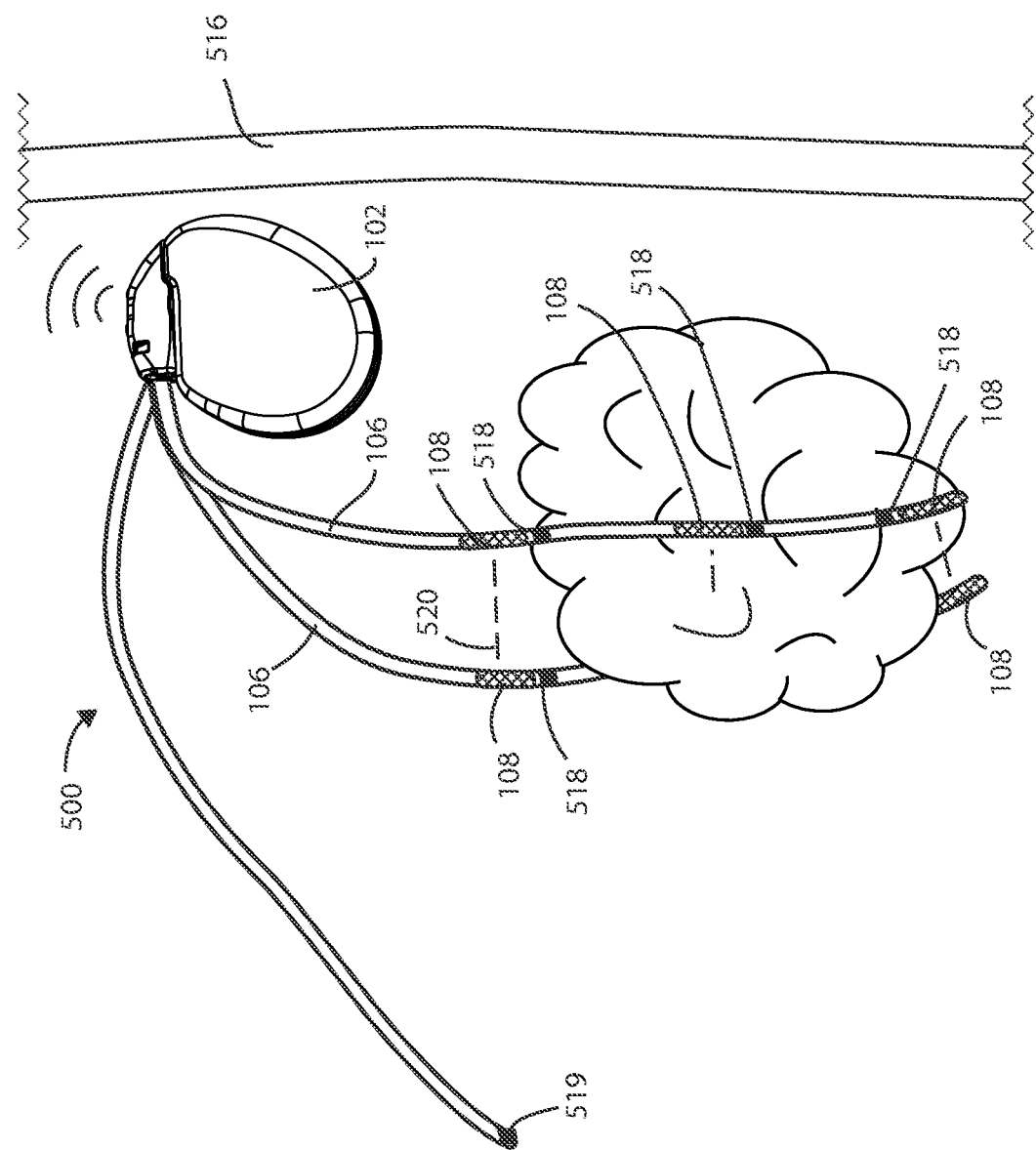
FIG. 5 is a schematic view of a medical device in accordance with various embodiments herein.

In reference now to FIG. 5, a schematic view of a medical device 500 is shown in accordance with various embodiments herein. In various embodiments, the medical device 500 can include at least one electric field generating circuit configured to generate one or more electric fields. The electric field generating circuit can be disposed within the housing 102. The medical device 500 can further include control circuitry that can be in communication with the electric field generating circuit. The control circuitry can be configured to control delivery of the one or more electric fields from the electric field generating circuit. In various embodiments, the control circuitry causes the electric field generating circuit to generate one or more electric fields at frequencies selected from a range of between 10 kHz to 1 MHz. In various embodiments, the medical device 500 can include an implanted housing 102. The implanted housing 102 can define an interior volume into which the electric field generating circuit and the first control circuit are disposed.

Figure 8:
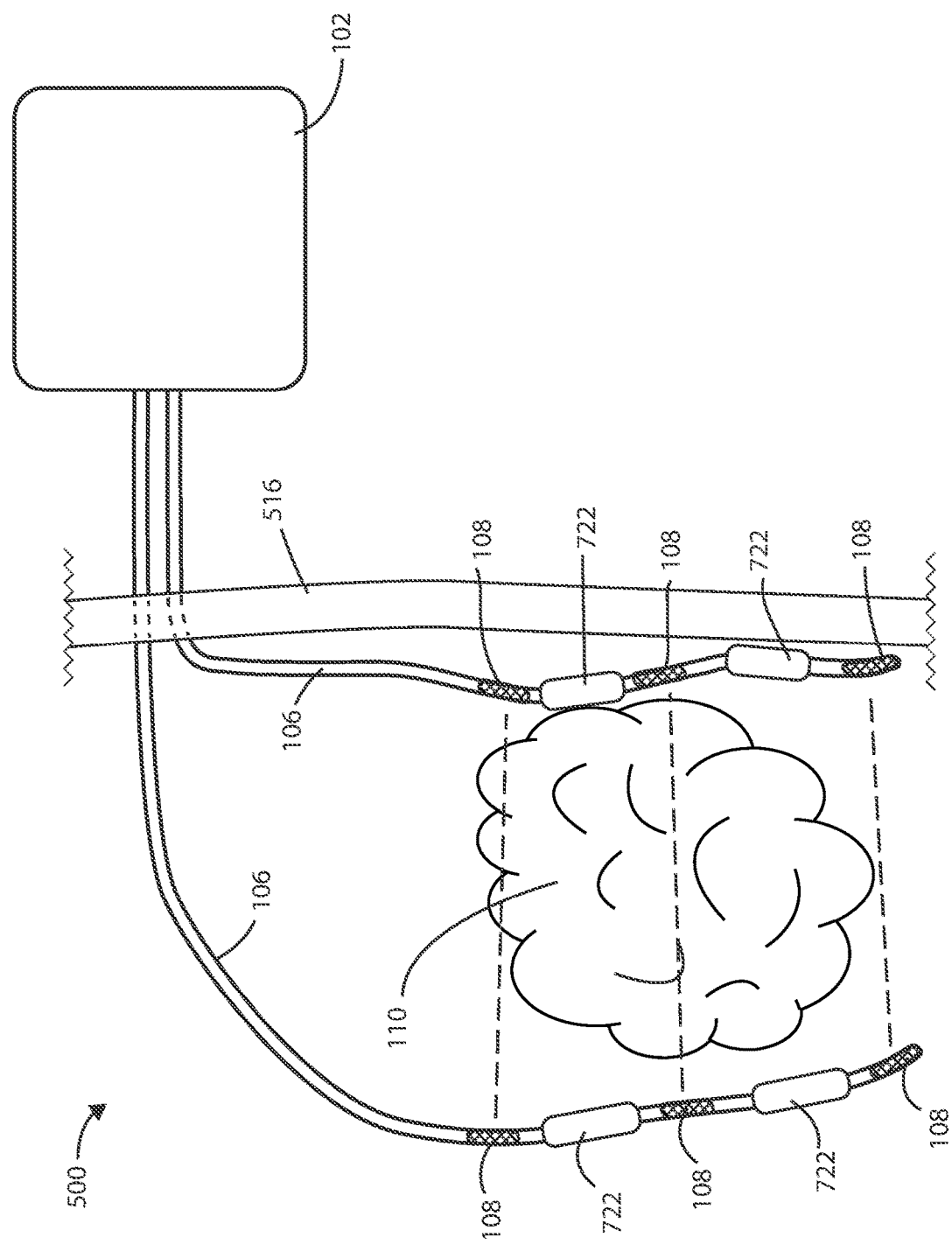
FIG. 8 is a schematic view of a medical device in accordance with various embodiments herein.

In some embodiments, the medical device 500 can include one or more leads 106, such as two leads 106 (although embodiments with three, four, five, six or more leads are also directly contemplated herein). In some embodiments, at least one of the leads 106 can be fully implanted or fully beneath the patient's skin 516, such as shown in FIG. 5. In some embodiments, a plurality of leads 106 are fully implanted, such as two leads 106, three leads 106, four leads 106, five leads 106, or six leads 106. In some embodiments, at least two electrodes 108 are implanted and disposed on a fully implanted lead 106. In various embodiments, the lead 106 can be a transcutaneous lead that extends across the patient's skin 516, such as shown in FIG. 8.

In various embodiments, the medical device 500 can include two or more electrodes 108. The electrodes 108 can be configured to deliver the electric fields to the site of a cancerous tumor 110. In various embodiments, a lead 106 can provide electrical communication between the control circuitry and at least one electrode 108. In various embodiments, an electric field can be delivered across at least one vector 520 defined by a pair of electrodes 108 formed by two or more electrodes 108. In some embodiments, the electric fields can be delivered across at least two vectors. In some embodiments, a first vector can be defined by a first pair of electrodes and a second vector can be defined by a second pair of electrodes.

Temperature Sensor

In some embodiments, the medical device can include at least one temperature sensor 518. The temperature sensor 518 can be configured to measure the temperature of tissue at the site of the tumor 110, such as to monitor temperature changes that could be a result of electric field generation or changes that could be a result of heating with a heating element. The temperature sensor 518 can be in electronic communication with the control circuitry. In some embodiments, the medical device can include at least one temperature sensor 519 which is disposed in tissue which is not within the region being treated, such as within healthy tissue. The temperature sensor 519, which is remote from the treatment region, can be used along with temperature sensors 518 to determine changes in temperature that are a result of the therapy.

Many different types of sensors can be used as a temperature sensor herein. In some embodiments, the temperature sensor 518 can be selected from the group consisting of a thermistor, a resistance thermometer, a thermocouple, a semi-conductor based sensor, a bimetallic device, a thermometer, a change-of-state sensor, an optical temperature sensor (such as an infrared sensor), and the like.

In some embodiments, the temperature sensor 518 can be disposed on a lead 106. In some embodiments, a plurality of temperature sensors 518 can be disposed on a single lead 106. In some embodiments, at least one temperature sensor 518 is disposed on each of the leads 106. In some embodiments with multiple leads 106, at least two of the leads 106 can have a temperature sensor 518 disposed on the lead 106.

In some embodiments herein, a temperature sensor can be chronically implanted. In some embodiments, a temperature sensor can be implanted for greater than 1, 2, 4, 8, 12, 24, 52 or more weeks, or an amount falling within a range between any of the foregoing. However, in some embodiments, a temperature sensor can be transitorily implanted. In some embodiments, a temperature sensor can be implanted for less than 2 days, 1 day, 12 hours, 4 hours, 2 hours, or 1 hour, or an amount falling within a range between any of the foregoing. In some embodiments, a temperature sensor 518 can be removable, such that it can be removed after confirmation that the medical device is delivering therapy in a safe or expected manner. In various embodiments, during implanting of the electrodes 108, a removeable temperature sensor can be implanted. The removeable temperature sensor can be configured to measure the temperature of tissue near one or more electrodes, such as during implanting the of the electrodes. The removeable temperature sensor can be mounted on a transitorily inserted lead, introducer sheath, guide wire, delivery catheter, other type of catheter, or other type of surgical or implant instrument.

In some embodiments, a patient can undergo a thermal scan, such as after a medical device has been implanted. The thermal scan can be conducted by an external device or component. The thermal scan can determine temperatures of tissues in the patient's body, such as tissues near the electrodes. The thermal scan can allow for a less intrusive manner to monitor the temperature of various tissues within the patient's body, such as during therapy by a medical device.

It will be appreciated that a thermal scan can be performed in various ways. For example, a thermal scan can be performed using infrared thermography (IRT), an infrared thermometer, thermal imaging, thermal video, indium antimonide (InSb) devices, mercury cadmium telluride (MCT) devices, and the like.

Temperature Estimation Based on Power Output

In some embodiments, the control circuitry can be configured to calculate the power output of the electric field. The control circuit can also be configured to estimate a temperature of tissue within the electric field, such as based on the power output and the distance between the electrodes 108 of the electrode pair. Power (in Watts) is related to current and resistance/impedance as follows $P_{avg}=I^2_{rms}*R$. 1 watt is equivalent to 1 joule/second. Heat transferred can be determined as $q=mC_p\Delta T$ or $\Delta T=q/mCp$, wherein q is energy in kilojoules, m is the mass, Cp is the specific heat capacity of the tissue, and $\Delta T$ is the change in temperature. Thus, $\Delta T$ can be approximated as $I^2_{rms}*R/mCp$. In some embodiments, the distance (D) between electrodes can be used as a proxy for mass. Thus, in some embodiments, $\Delta T$ can be approximated as $I^2_{rms}*R/DCp$. The specific heat capacity of the tissue can be about 3.6 to 3.9 $kg^{-1}K^{-1}$.

In some embodiments, the control circuit can be configured to estimate a power output based on a change in temperature. Specifically, the equations above can reconfigure to solve for $P_{avg}$ based on $\Delta T$.

In some embodiments, the medical device 500 can be configured to receive data regarding the distance between two electrodes 108 in an electrode pair, such as to estimate the temperature of the tissue within the electric field. In some embodiments, the medical device 500 can receive data regarding the distance between two electrodes from a user. As an example, a user can enter the distance during a programming phase. In some embodiments, a user, such as a physician, can use an imaging device, such as a fluoroscope or ultrasound imaging device, to determine the distance between two electrodes 108. The data can then be entered into the medical device 500. In further embodiments, the medical device 500 can be configured to estimate the distance between the electrodes 108 of an electrode pair, such as based on impedance data between the two electrodes 108.

Temperature as a Function of Impedance

In some embodiments, the control circuitry can be configured to estimate the temperature of tissue within the electric field, such as based on an impedance measurement. In some embodiments, the control circuitry can be configured to estimate the temperature of tissue within the electric field, such as based on an impedance measurement and the distance between the electrodes 108 of the electrode pair. The medical device 500 can be configured to receive data regarding the distance between the electrodes 108 of the electrode pair. In further embodiments, the control circuitry can be configured to estimate changes in temperature of tissue within the electric field, such as based on changes in measured impedance.

In various embodiments, the impedance of tissue can change as the temperature of the tissue changes. These changes in impedance can be characterized and compared to known data for the therapy device. Afterwards, the impedance measurements can be correlated to a temperature estimate of the tissue.

Figure 6:
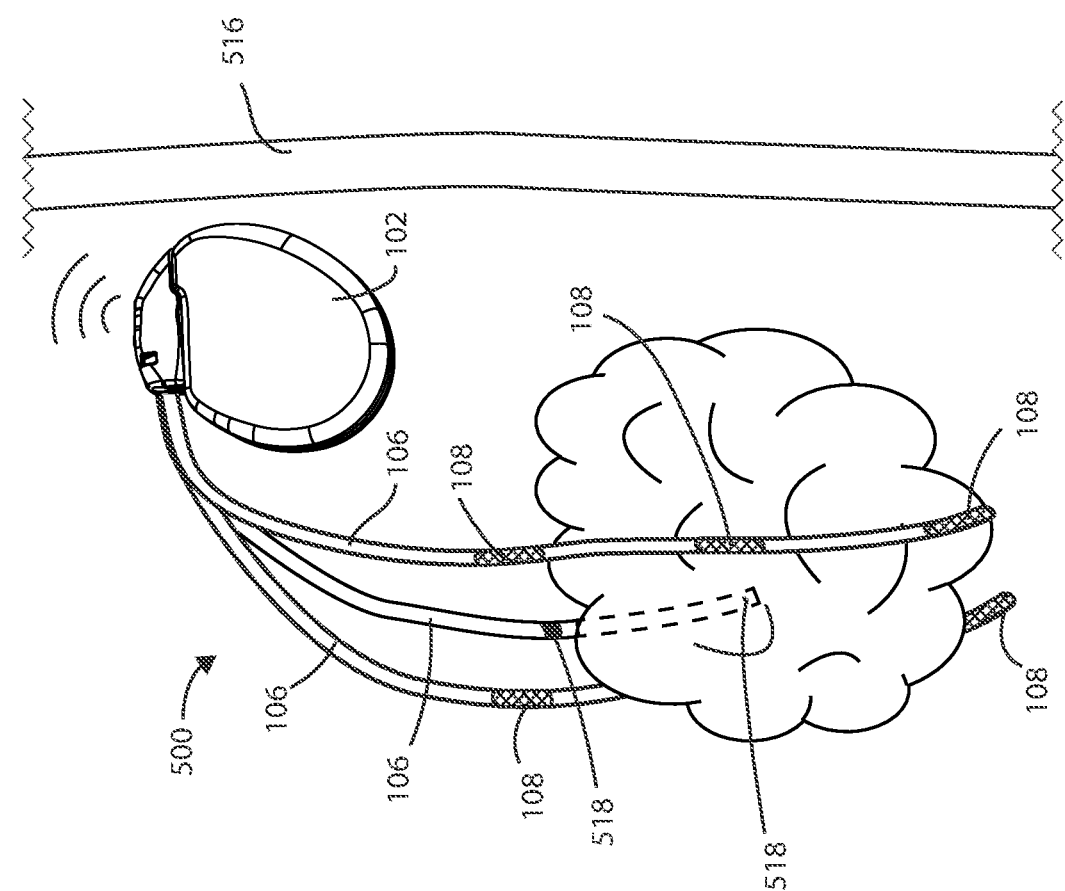
FIG. 6 is a schematic view of a medical device in accordance with various embodiments herein.

In reference now to FIG. 6, a schematic view of a medical device 500 is shown in accordance with various embodiments herein. In some embodiments, the medical device 500 can include a temperature sensor 518 positioned between a pair of electrodes 108. In some embodiments, the temperature sensor 518 can be adapted to be inserted into the tumor 110.

In some embodiments, the lead 106 which the temperature sensor 518 is disposed on does not include an electrode. In some embodiments, the lead 106 can include a plurality of temperature sensors 518.

Heating Therapy

Figure 7:
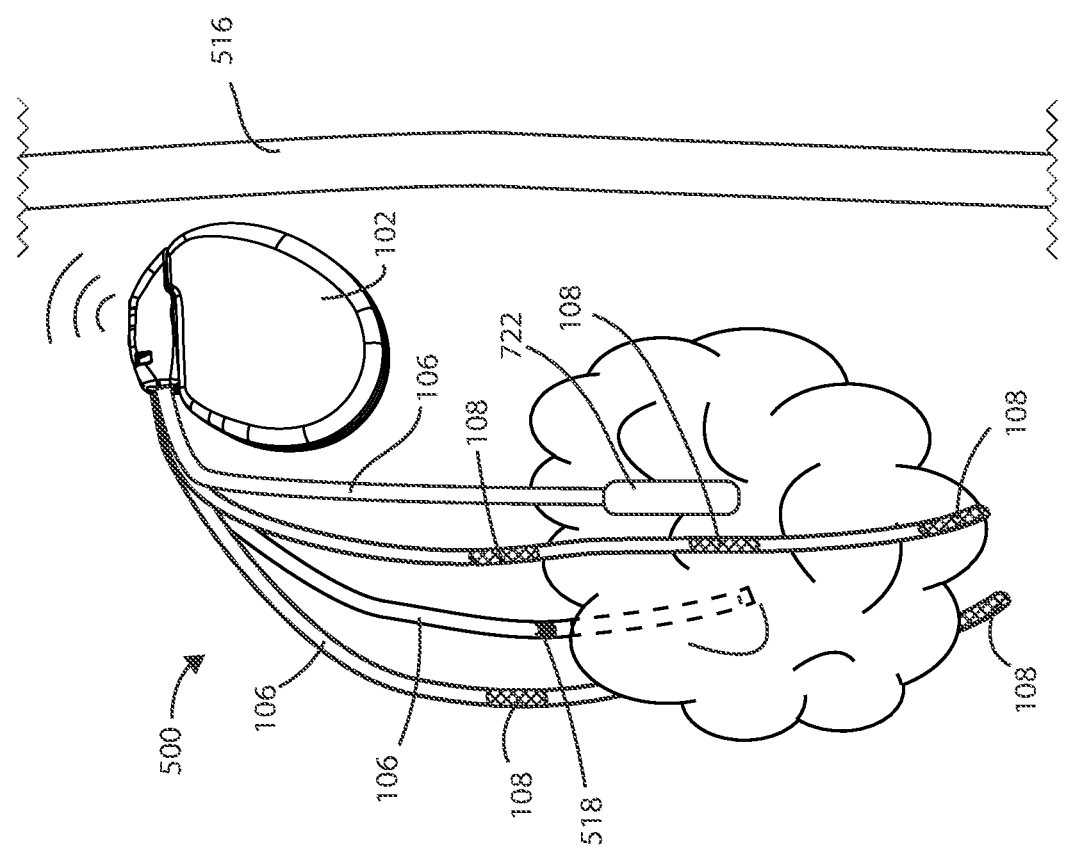
FIG. 7 is a schematic view of a medical device in accordance with various embodiments herein.

In some embodiments, the therapy delivered by the medical device 500 can include generating an electric field and generating heat at the tumor 110. FIG. 7 is a schematic view of a medical device 500 in accordance with various embodiments herein. In some embodiments, the medical device 500 can include a heating element 722. The heating element 722 can be configured to generate heat. In various embodiments, the heating element 722 can generate heat simultaneously with the electrodes generating an electric field.

The heating element 722 can generate heat and cause tissue to be heated through various means. In some embodiments, the heating element 722 may operate to heat tissue through conduction. For example, the heating element 722 may itself heat up through joule heating (also known as Ohmic or resistive heating) which can be performed by passing an electric current through a component with electrical resistance. For example, a nichrome (nickel/chromium 80/20) wire, ribbon, or strip either directly exposed or embedded within another material can be used as a heating element 722 and as it is heated it can heat the surrounding tissue through thermal conduction. Various other materials can also be used as a heating element. In some embodiments, the heating element 722 may emit electromagnetic radiation that is then absorbed by the surrounding tissue causing it to heat up. For example, the heating element 722 can include an infrared light emitter which generates electromagnetic radiation that can be absorbed the surrounding tissue raising its temperature, which can serve as an example of radiant heating. In some embodiments, the heating element 722 can provide heat to tissue both through conduction and radiation.

In some embodiments, the control circuitry causes the heating element 722 to generate heat. In some embodiments, the control circuitry estimates the temperature of tissue within the electric field based on an impedance measurement. In some embodiments, the control circuitry estimates the temperature of the tissue within the electric field based on a power measurement.

In various embodiments, one or more heating elements 722 can be disposed on a lead 106. In some embodiments, a lead 106 which includes a heating element 722 does not include an electrode 108.

In some embodiments, a lead 106 can include at least one heating element 722 and at least one electrode 108, such as shown in FIG. 8. FIG. 8 shows a schematic view of a medical device 500 in accordance with various embodiments herein. The medical device 500 can include a housing 102 (which can be an external housing in this example) and one or more leads 106.

The medical device 500 can include one or more transcutaneous leads 106, such as a lead 106 that passes through or across the patient's skin 516. In various embodiments, at least two electrodes 108 are implanted and disposed on a transcutaneous lead 106. In various embodiments, at least two electrodes 108 are implanted and disposed on transcutaneous leads 106, such as at least one electrode 108 on two different transcutaneous leads 106.

External Power Source

In some cases, device operations herein may consume a significant amount of electrical power. By way of example, joule heating may consume a significant amount of electrical power. The power capacity of fully implanted components may be somewhat limited (e.g., there are finite limits to the total power capacity provided by implanted batteries). As such, in some embodiments, the system may be configured to deliver power to an internal (implanted) component from an external power source.

Figure 9:
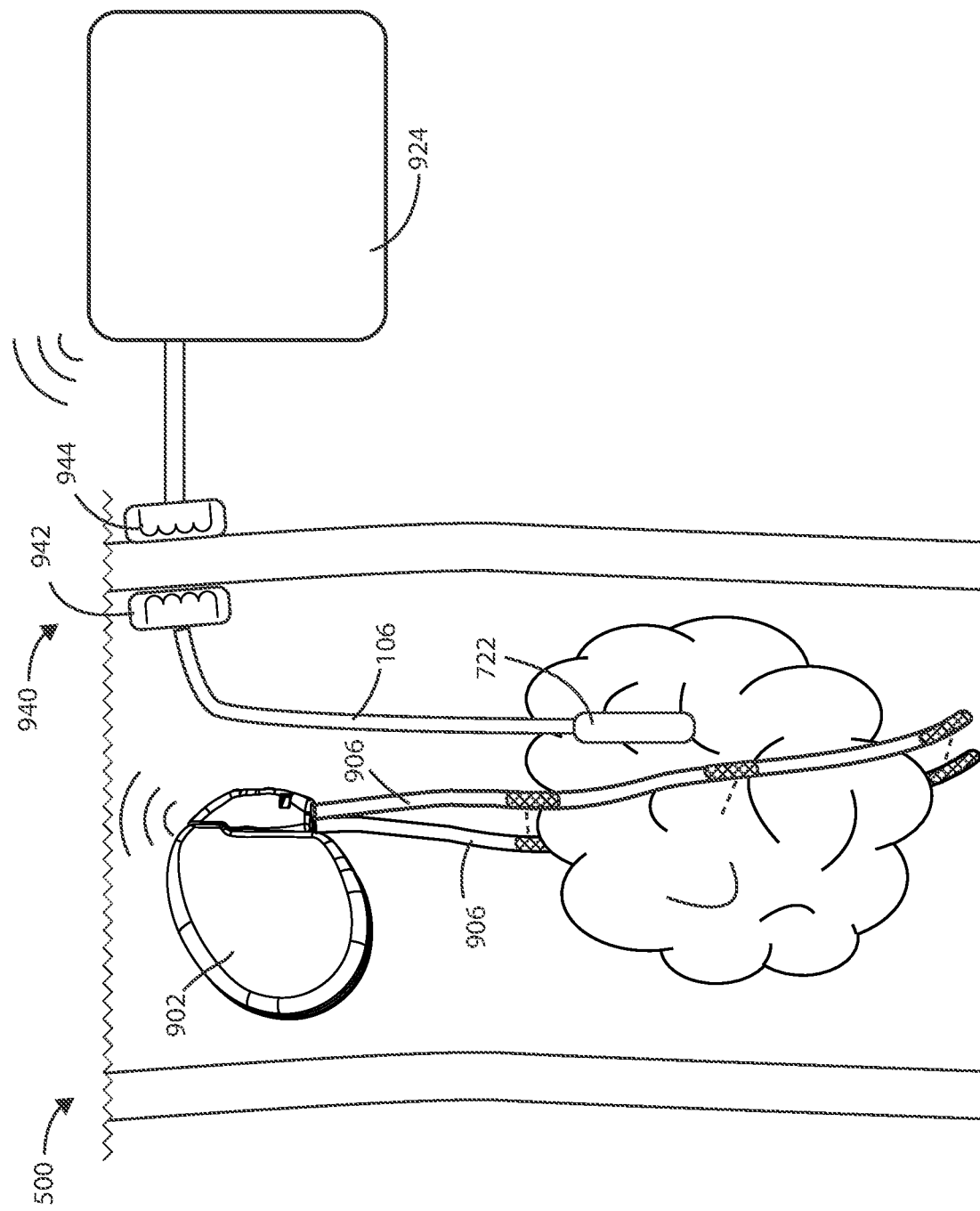
FIG. 9 is a schematic view of a medical device in accordance with various embodiments herein.

FIG. 9 show a schematic view of a medical device 500 in accordance with various embodiments herein. The medical device 500 can include an implanted housing 902 and one or more fully implanted leads 906. The implanted leads 906 can include electrodes 108. The medical device 500 can include an external housing 924. In some embodiments, an external power supply can be disposed within the external housing 924. In various embodiments, the implanted housing 902 can be in wireless communication with the external housing 924, such as exchange data or information regarding therapy delivery.

In some embodiments, control circuitry can be disposed in one of the implanted housing 902 or the external housing 924. In some embodiments, control circuitry can be disposed at least partially in the implanted housing 902 and the external housing 924.

In some embodiments, a transcutaneous lead 106 can include a wireless power transfer connection 940. The wireless power transfer connection 940 can be established transcutaneously between the external housing 924, such as a power supply within an external housing 924, and an implanted lead 106. In some embodiments, the medical device 500 can include an inductive power transfer link, including paired internal 942 and external 944 inductors to transfer power form outside of the body to an implanted component of the system. The inductive power transfer link can allow for a transfer of power from an external power supply to an internal component, which in turn can cause an electrical field to be generated or heat to be generated without puncturing the skin 516 or otherwise requiring a maintained opening or tunnel through the patient's skin 516.

In various embodiments, the fully implanted leads 906 can include electrodes 108 and can be free of heating elements 722, and the transcutaneous lead 106 can include one or more heating elements 722. In some embodiments, the external housing 924 can include a power source, such as to power the heating elements 722.

Figure 10:
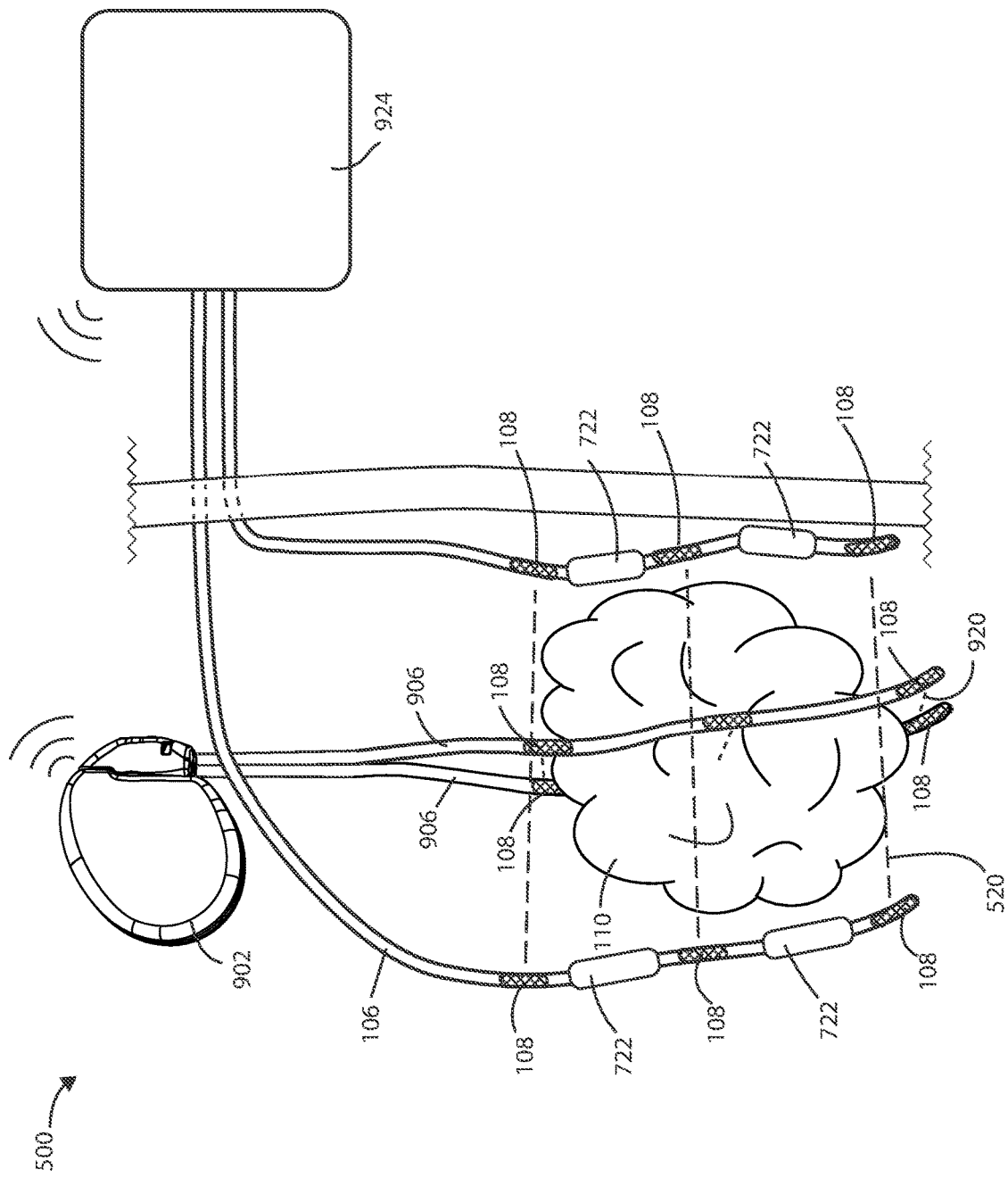
FIG. 10 is a schematic view of a medical device in accordance with various embodiments herein.

In reference now to FIG. 10 a schematic view of a medical device 500 is shown in accordance with various embodiments herein. In some embodiments, the electric fields can be delivered across at least two vectors 520, 920. The first vector 520 can be defined by a first pair of electrodes 108, and the second vector 920 can be defined by a second pair of electrodes 108. In various embodiments, the first vector 520 and the second vector 920 can be substantially orthogonal to one another.

In some embodiments, the medical device 500 can include at least two electric field generating circuits. In various embodiments, a first electric field generating circuit can be implanted, such as within the housing 902, and a second electric field generating circuit can be external, such as within the housing 924.

Figure 11:
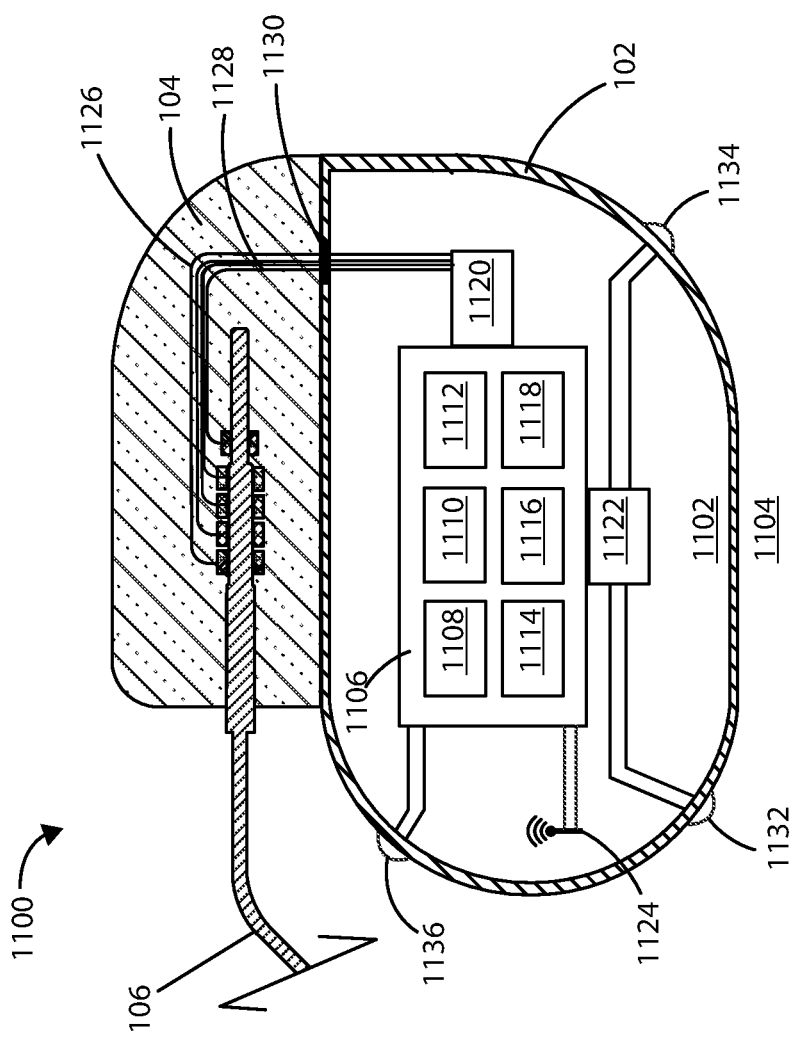
FIG. 11 is a schematic cross-sectional view of a medical device in accordance with various embodiments herein.

Referring now to FIG. 11, a schematic cross-sectional view of medical device 1100 is shown in accordance with various embodiments herein. The housing 102 can define an interior volume 1102 that can be hollow and that in some embodiments is hermetically sealed off from the area 1104 outside of medical device 1100. In other embodiments the housing 102 can be filled with components and/or structural materials such that it is non-hollow. The medical device 1100 can include control circuitry 1106, which can include various components 1108, 1110, 1112, 1114, 1116, and 1118 disposed within housing 102. In some embodiments, these components can be integrated and in other embodiments these components can be separate. In yet other embodiments, there can be a combination of both integrated and separate components. The medical device 1100 can also include an antenna 1124, to allow for unidirectional or bidirectional wireless data communication, such as with an external device or an external power supply. In some embodiments, the components of medical device 1100 can include an inductive energy receiver coil (not shown) communicatively coupled or attached thereto to facilitate transcutaneous recharging of the medical device via recharging circuitry.

The various components 1108, 1110, 1112, 1114, 1116, and 1118 of control circuitry 1106 can include, but are not limited to, a microprocessor, memory circuit (such as random access memory (RAM) and/or read only memory (ROM)), recorder circuitry, controller circuit, a telemetry circuit, a power supply circuit (such as a battery), a timing circuit, and an application specific integrated circuit (ASIC), a recharging circuit, amongst others. Control circuitry 1106 can be in communication with an electric field generating circuit 1120 that can be configured to generate electric current to create one or more fields. The electric field generating circuit 1120 can be integrated with the control circuitry 1106 or can be a separate component from control circuitry 1106. Control circuitry 1106 can be configured to control delivery of electric current from the electric field generating circuit 1120. In some embodiments, the electric field generating circuit 1120 can be present in a portion of the medical device that is external to the body.

In some embodiments, the control circuitry 1106 can be configured to direct the electric field generating circuit 1120 to deliver an electric field via leads 106 to the site of a cancerous tumor located within a bodily tissue. In other embodiments, the control circuitry 1106 can be configured to direct the electric field generating circuit 1120 to deliver an electric field via the housing 102 of medical device 1100 to the site of a cancerous tumor located within a bodily tissue. In other embodiments, the control circuitry 1106 can be configured to direct the electric field generating circuit 1120 to deliver an electric field between leads 106 and the housing 102 of medical device 1100. In some embodiments, one or more leads 106 can be in electrical communication with the electric field generating circuit 1120.

In some embodiments, various components within medical device 1100 can include an electric field sensing circuit 1122 configured to generate a signal corresponding to sensed electric fields. Electric field sensing circuit 1122 can be integrated with control circuitry 1106 or it can be separate from control circuitry 1106.

Sensing electrodes can be disposed on or adjacent to the housing of the medical device, on one or more leads connected to the housing, on a separate device implanted near or in the tumor, or any combination of these locations. In some embodiments, the electric field sensing circuit 1122 can include a first sensing electrode 1132 and a second sensing electrode 1134. In other embodiments, the housing 102 itself can serve as a sensing electrode for the electric field sensing circuit 1122. The electrodes 1132 and 1134 can be in communication with the electric field sensing circuit 1122. The electric field sensing circuit 1122 can measure the electrical potential difference (voltage) between the first electrode 1132 and the second electrode 1134. In some embodiments, the electric field sensing circuit 1122 can measure the electrical potential difference (voltage) between the first electrode 1132 or second electrode 1134, and an electrode disposed along the length of one or more leads 106. In some embodiments, the electric field sensing circuit can be configured to measure sensed electric fields and to record electric field strength in V/cm.

It will be appreciated that the electric field sensing circuit 1122 can additionally measure an electrical potential difference between the first electrode 1132 or the second electrode 1134 and the housing 102 itself. In other embodiments, the medical device can include a third electrode 1136, which can be an electric field sensing electrode or an electric field generating electrode. In some embodiments, one or more sensing electrodes can be disposed along lead 106 and can serve as additional locations for sensing an electric field. Many combinations can be imagined for measuring electrical potential difference between electrodes disposed along the length of one or more leads 106 and the housing 102 in accordance with the embodiments herein.

In some embodiments, the one or more leads 106 can be in electrical communication with the electric field generating circuit 1120. The one or more leads 106 can include one or more electrodes 108, as shown in FIGS. 1 and 2. In some embodiments, various electrical conductors, such as electrical conductors 1126 and 1128, can pass from the header 104 through a feed-through structure 1130 and into the interior volume 1102 of medical device 1100. As such, the electrical conductors 1126 and 1128 can serve to provide electrical communication between the one or more leads 106 and control circuitry 1106 disposed within the interior volume 1102 of the housing 102.

In some embodiments, recorder circuitry can be configured to record the data produced by the electric field sensing circuit 1122 and record time stamps regarding the same. In some embodiments, the control circuitry 1106 can be hardwired to execute various functions, while in other embodiments the control circuitry 1106 can be directed to implement instructions executing on a microprocessor or other external computation device. A telemetry circuit can also be provided for communicating with external computation devices such as a programmer, a home-based unit, and/or a mobile unit (e.g. a cellular phone, personal computer, smart phone, tablet computer, and the like).

Figure 12:
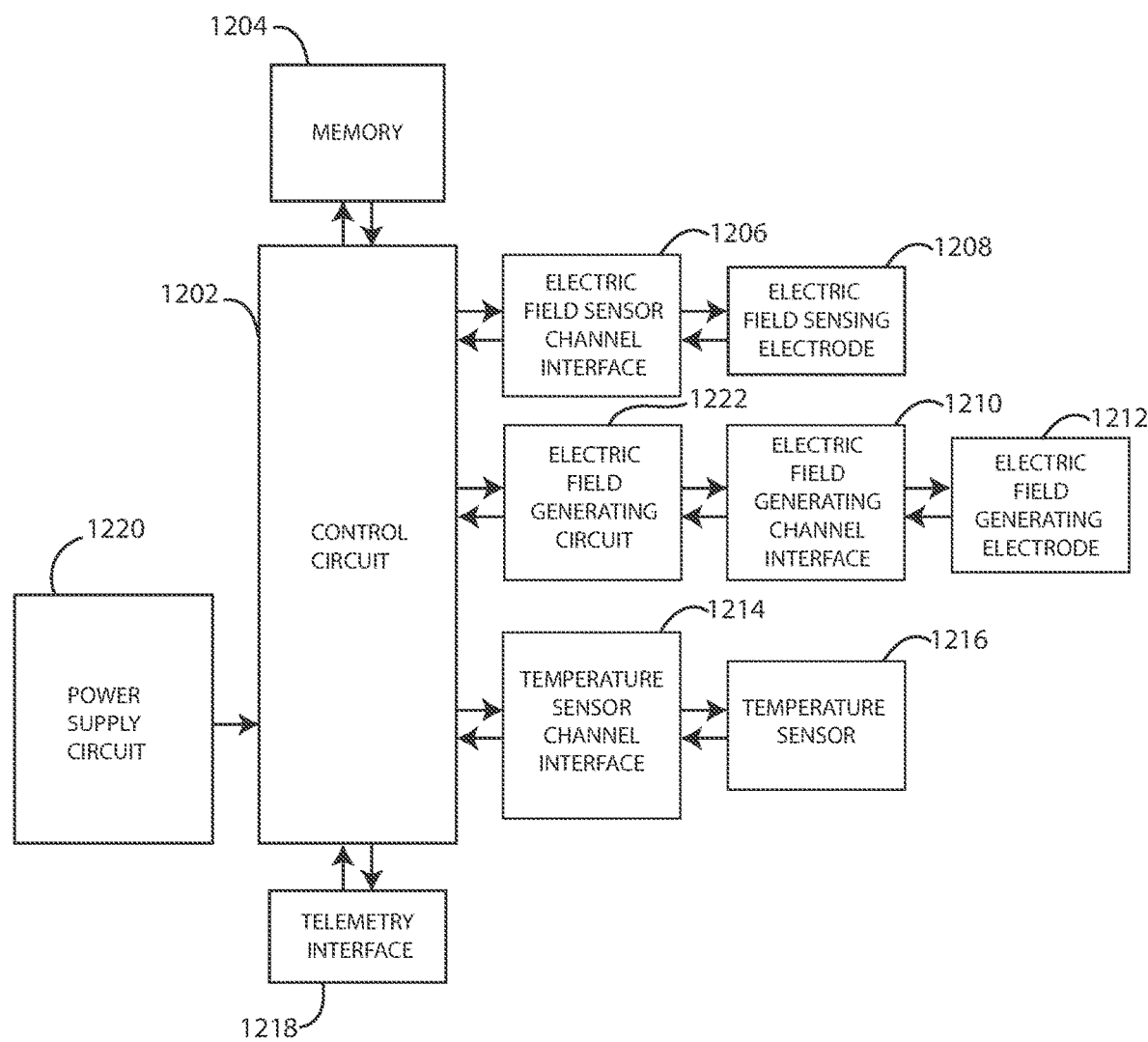
FIG. 12 is a schematic diagram of components of a medical device in accordance with various embodiments herein.

Elements of various embodiments of the medical devices described herein are shown in FIG. 12. However, it will be appreciated that some embodiments can include additional elements beyond those shown in FIG. 12. In addition, some embodiments may lack some elements shown in FIG. 12. The medical devices as embodied herein can gather information through one or more sensing channels and can output information through one or more field generating channels. A microprocessor 1202 can communicate with a memory 1204 via a bidirectional data bus. The memory 1204 can include read only memory (ROM) or random-access memory (RAM) for program storage and RAM for data storage. The microprocessor 1202 can also be connected to a telemetry interface 1218 for communicating with external devices such as a programmer, a home-based unit and/or a mobile unit (e.g. a cellular phone, personal computer, smart phone, tablet computer, and the like) or directly to the cloud or another communication network as facilitated by a cellular or other data communication network. The medical device can include a power supply circuit 1220. In some embodiments, the medical device can include an inductive energy receiver coil interface (not shown) communicatively coupled or attached thereto to facilitate transcutaneous recharging of the medical device.

The medical device can include one or more electric field sensing electrodes 1208 and one or more electric field sensor channel interfaces 1206 that can communicate with a port of microprocessor 1202. The medical device can also include one or more electric field generating circuits 1222, one or more electric field generating electrodes 1212, and one or more electric field generating channel interfaces 1210 that can communicate with a port of microprocessor 1202. The medical device can also include one or more temperature sensors 1216 and one or more temperature sensor channel interfaces 1214 that can communicate with a port of microprocessor 1202. The channel interfaces 1206, 1210, and 1214 can include various components such as analog-to-digital converters for digitizing signal inputs, sensing amplifiers, registers which can be written to by the control circuitry in order to adjust the gain and threshold values for the sensing amplifiers, source drivers, modulators, demodulators, multiplexers, and the like.

Although the temperature sensors 1216 are shown as part of a medical device in FIG. 12, it is realized that in some embodiments one or more of the temperature sensors could be physically separate from the medical device. In various embodiments, one or more of the temperature sensors can be within another implanted medical device communicatively coupled to a medical device via telemetry interface 1218. In yet other embodiments, one or more of the temperature sensors can be external to the body and coupled to a medical device via telemetry interface 1218.

Methods

Many different methods are contemplated herein, including, but not limited to, methods of making, methods of using, and the like. Aspects of system/device operation described elsewhere herein can be performed as operations of one or more methods in accordance with various embodiments herein.

In an embodiment, a method of treating a cancerous tumor is included. The method can include implanting at least two electrodes inside a body of a patient with the cancerous tumor, implanting a temperature sensor inside the body of the patent, generating an electrical field between at least one pair of electrodes, the electric field having frequencies within a range of between 10 kHz to 1 MHz, and sensing the temperature with the temperature sensor.

Figure 13:
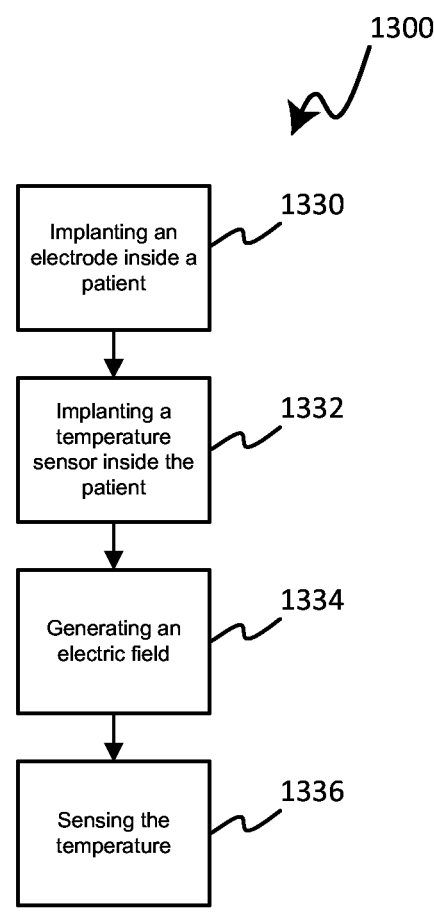
FIG. 13 is a flowchart depicting a method in accordance with various embodiments herein.

FIG. 13 shows a flowchart depicting a method 1300 in accordance with various embodiments herein. The method 1300 can be a method for treating a cancerous tumor. The method 1300 can include implanting at least two electrodes inside a body of a patient with the cancerous tumor, step 1330. The method 1300 can further include implanting a temperature sensor inside the body of the patent, step 1332, such as near or within the cancerous tumor. The method 1300 can also include generating an electrical field between at least one pair of electrodes, step 1334. In various embodiments, the electric field can have frequencies within a range of between 10 kHz to 1 MHz.

In some embodiments, the method 1300 can include sensing the temperature with the temperature sensor, step 1336, such as the temperature of the tissue near the tumor or the temperature of the tumor. In some embodiments, the method 1300 can include estimating the temperature of tissue within the electric field, such as based on the power output and the distance between the electrodes. In some embodiments, the method 1300 can include estimating the distance between electrodes of an electrode pair, such as based on impedance data.

Electrical Stimulation Parameters

In various embodiments, systems or device herein (or components thereof, such as control circuitry) can be configured to direct an electric field generating circuit to deliver an electric field using one or more frequencies selected from a range of between 10 kHz to 1 MHz. In some embodiments, the control circuitry can be configured to direct the electric field generating circuit to deliver an electric field at one or more frequencies selected from a range of between 100 kHz to 500 kHz. In some embodiments, the control circuitry can be configured to direct the electric field generating circuit to deliver an electric field at one or more frequencies selected from a range of between 100 kHz to 300 kHz. In some embodiments, the control circuitry can be configured to direct the electric field generating circuit to periodically deliver an electric field using one or more frequencies greater than 1 MHz.

In some embodiments, the electric field can be effective in disrupting cellular mitosis in cancerous cells. The electric field can be delivered to the site of a cancerous tumor along more than one vector. In some examples, the electric field can be delivered along at least one vector, including at least one of the lead electrodes. In some embodiments, at least two vectors with spatial diversity between the two vectors can be used. The vectors can be spatially and/or directionally separated (e.g., the vectors can be disposed at an angle with respect to one another) by at least about 10, 20, 30, 40, 50, 60, 70, 80 or 90 degrees.

A desired electric field strength can be achieved by delivering an electric current between two electrodes. The specific current and voltage at which the electric field is delivered can vary and can be adjusted to achieve the desired electric field strength at the site of the tissue to be treated. In some embodiments, the control circuitry can be configured to direct the electric field generating circuit to deliver an electric field using currents ranging from 1 mAmp to 1000 mAmp to the site of a cancerous tumor. In some embodiments, the control circuitry can be configured to direct the electric field generating circuit to deliver an electric field using currents ranging from 20 mAmp to 500 mAmp to the site of a cancerous tumor. In some embodiments, the control circuitry can be configured to direct the electric field generating circuit to deliver an electric field using currents ranging from 30 mAmp to 300 mAmp to the site of a cancerous tumor.

In some embodiments, the control circuitry can be configured to direct the electric field generating circuit to deliver an electric field using currents including 1 mAmp, 2 mAmp, 3 mAmp, 4 mAmp, 5 mAmp, 6 mAmp, 7 mAmp, 8 mAmp, 9 mAmp, 10 mAmp, 15 mAmp, 20 mAmp, 25 mAmp, 30 mAmp, 35 mAmp, 40 mAmp, 45 mAmp, 50 mAmp, 60 mAmp, 70 mAmp, 80 mAmp, 90 mAmp, 100 mAmp, 125 mAmp, 150 mAmp, 175 mAmp, 200 mAmp, 225 mAmp, 250 mAmp, 275 mAmp, 300 mAmp, 325 mAmp, 350 mAmp, 375 mAmp, 400 mAmp, 425 mAmp, 450 mAmp, 475 mAmp, 500 mAmp, 525 mAmp, 550 mAmp, 575 mAmp, 600 mAmp, 625 mAmp, 650 mAmp, 675 mAmp, 700 mAmp, 725 mAmp, 750 mAmp, 775 mAmp, 800 mAmp, 825 mAmp, 850 mAmp, 875 mAmp, 900 mAmp, 925 mAmp, 950 mAmp, 975 mAmp, or 1000 mAmp. It will be appreciated that the control circuitry can be configured to direct the electric field generating circuit to deliver an electric field at a current falling within a range, wherein any of the forgoing currents can serve as the lower or upper bound of the range, provided that the lower bound of the range is a value less than the upper bound of the range.

In some embodiments, the control circuitry can be configured to direct the electric field generating circuit to deliver an electric field using voltages ranging from 1 $V_{rms}$ to 50 $V_{rms}$ to the site of a cancerous tumor. In some embodiments, the control circuitry can be configured to direct the electric field generating circuit to deliver an electric field using voltages ranging from 5 $V_{rms}$ to 30 $V_{rms}$ to the site of a cancerous tumor. In some embodiments, the control circuitry can be configured to direct the electric field generating circuit to deliver an electric field using voltages ranging from 10 $V_{rms}$ to 20 $V_{rms}$ to the site of a cancerous tumor.

In some embodiments, the control circuitry can be configured to direct the electric field generating circuit to deliver an electric field using one or more voltages including 1 $V_{rms}$, 2 $V_{rms}$, 3 $V_{rms}$, 4 $V_{rms}$, 5 $V_{rms}$, 6 $V_{rms}$, 7 $V_{rms}$, 8 $V_{rms}$, 9 $V_{rms}$, 10 $V_{rms}$, 15 $V_{rms}$, 20 $V_{rms}$, 25 $V_{rms}$, 30 $V_{rms}$, 35 $V_{rms}$, 40 $V_{rms}$, 45 $V_{rms}$, or 50 $V_{rms}$. It will be appreciated that the control circuitry can be configured to direct the electric field generating circuit to deliver an electric field using a voltage falling within a range, wherein any of the forgoing voltages can serve as the lower or upper bound of the range, provided that the lower bound of the range is a value less than the upper bound of the range.

In some embodiments, the control circuitry can be configured to direct the electric field generating circuit to deliver and electric field using one or more frequencies including 10 kHz, 20 kHz, 30 kHz, 40 kHz, 50 kHz, 60 kHz, 70 kHz, 80 kHz, 90 kHz, 100 kHz, 125 kHz, 150 kHz, 175 kHz, 200 kHz, 225 kHz, 250 kHz, 275 kHz, 300 kHz, 325 kHz, 350 kHz, 375 kHz, 400 kHz, 425 kHz, 450 kHz, 475 kHz, 500 kHz, 525 kHz, 550 kHz, 575 kHz, 600 kHz, 625 kHz, 650 kHz, 675 kHz, 700 kHz, 725 kHz, 750 kHz, 775 kHz, 800 kHz, 825 kHz, 850 kHz, 875 kHz, 900 kHz, 925 kHz, 950 kHz, 975 kHz, 1 MHz. It will be appreciated that the electric field generating circuit can deliver an electric field using a frequency falling within a range, wherein any of the foregoing frequencies can serve as the upper or lower bound of the range, provided that the upper bound is greater than the lower bound.

In some embodiments, the control circuitry can be configured to direct the electric field generating circuit to generate one or more applied electric field strengths selected from a range of between 0.25 V/cm to 1000 V/cm. In some embodiments, the control circuitry can be configured to direct the electric field generating circuit to generate one or more applied electric field strengths of greater than 3 V/cm. In some embodiments, the control circuitry can be configured to direct the electric field generating circuit to generate one or more applied electric field strengths selected from a range of between 1 V/cm to 10 V/cm. In some embodiments, the control circuitry can be configured to direct the electric field generating circuit to generate one or more applied electric field strengths selected from a range of between 3 V/cm to 5 V/cm.

In other embodiments, the control circuitry can be configured to direct the electric field generating circuit to generate one or more applied electric field strengths including 0.25 V/cm, 0.5 V/cm, 0.75 V/cm, 1.0 V/cm, 2.0 V/cm, 3.0 V/cm, 5.0 V/cm, 6.0 V/cm, 7.0 V/cm, 8.0 V/cm, 9.0 V/cm, 10.0 V/cm, 20.0 V/cm, 30.0 V/cm, 40.0 V/cm, 50.0 V/cm, 60.0 V/cm, 70.0 V/cm, 80.0 V/cm, 90.0 V/cm, 100.0 V/cm, 125.0 V/cm, 150.0 V/cm, 175.0 V/cm, 200.0 V/cm, 225.0 V/cm, 250.0 V/cm, 275.0 V/cm, 300.0 V/cm, 325.0 V/cm, 350.0 V/cm, 375.0 V/cm, 400.0 V/cm, 425.0 V/cm, 450.0 V/cm, 475.0 V/cm, 500.0 V/cm, 600.0 V/cm, 700.0

V/cm, 800.0 V/cm, 900.0 V/cm, 1000.0 V/cm. It will be appreciated that the electric field generating circuit can generate an electric field having a field strength at a treatment site falling within a range, wherein any of the foregoing field strengths can serve as the upper or lower bound of the range, provided that the upper bound is greater than the lower bound.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A medical device system comprising:
an electric field generating circuit configured to generate one or more electric fields; and
a control circuit in communication with the electric field generating circuit, the control circuit configured to control delivery of the one or more electric fields from the electric field generating circuit;
two or more electrodes forming at least one electrode pair to deliver the one or more electric fields to a site of a cancerous tumor within a patient; and
wherein the control circuit causes the electric field generating circuit to generate the one or more electric fields at frequencies selected from a range of between 10 kHz to 1 MHz, wherein the one or more electric fields are effective to disrupt cellular mitosis in a cancerous cell;
wherein the control circuit calculates a power output of the one or more electric fields and estimates a temperature of tissue within the one or more electric fields based on the power output and a distance between the two or more electrodes of the at least one electrode pair;
wherein the temperature of the tissue is estimated by dividing an average power output by the product of the distance between the two or more electrodes and a specific heat capacity of the tissue.

2. The medical device system of claim 1, wherein the medical device system is configured to receive data regarding the distance between the two or more electrodes of the at least one electrode pair.

3. The medical device system of claim 1, wherein the medical device system is configured to estimate the distance between the two or more electrodes of the at least one electrode pair based on impedance data.

4. The medical device system of claim 2, wherein the medical device system receives the data regarding the distance between the two more electrodes from a user.

5. The medical device system of claim 4, wherein the user determines the distance between the two or more electrodes using equipment selected from the group consisting of an imaging device, a fluoroscope, and an ultrasound imaging device.

* * * * *